(12) United States Patent
Shine

(10) Patent No.: US 9,932,570 B2
(45) Date of Patent: Apr. 3, 2018

(54) ANTHRAX LETHAL FACTOR SUBSTRATES AND METHODS OF USE THEREOF

(71) Applicant: List Biological Laboratories, Inc., Campbell, CA (US)

(72) Inventor: Nancy Shine, Campbell, CA (US)

(73) Assignee: List Biological Laboratories, Inc., Campbell, CA (US)

( * ) Notice: Subject to any disclaimer, the term of this patent is extended or adjusted under 35 U.S.C. 154(b) by 0 days.

(21) Appl. No.: 15/216,556

(22) Filed: Jul. 21, 2016

(65) Prior Publication Data

US 2017/0114338 A1    Apr. 27, 2017

Related U.S. Application Data

(60) Provisional application No. 62/245,736, filed on Oct. 23, 2015.

(51) Int. Cl.
*C12N 9/54* (2006.01)
*G01N 33/573* (2006.01)

(52) U.S. Cl.
CPC ........ *C12N 9/54* (2013.01); *C12Y 304/24083* (2013.01); *G01N 33/573* (2013.01); *G01N 2333/954* (2013.01)

(58) Field of Classification Search
None
See application file for complete search history.

(56) References Cited

U.S. PATENT DOCUMENTS

| | | | |
|---|---|---|---|
| 7,410,769 B2 | 8/2008 | Burroughs-Tencza | |
| 8,663,926 B2 * | 3/2014 | Boyer | G01N 33/56911 424/246.1 |
| 2008/0033025 A1 * | 2/2008 | Pellecchia | A61K 31/427 514/369 |
| 2012/0122123 A1 | 5/2012 | Boyer et al. | |

FOREIGN PATENT DOCUMENTS

WO    2015038784    3/2015

OTHER PUBLICATIONS

Mahalakshmi et al. 2006 (The use of D-amino acids in peptide design; in D-Amino Acids: A new Fronteir in Amino Acid and Protein Research; Nova Science Publishers; ISBN: 1-60021-075-9).*

Boyer AE, et al., (2007) "Detection and quantification of anthrax lethal factor in serum by mass spectrometry", Anal Chem, 79:8463-8470.

Boyer AE, et al., (2011) "High-sensitivity MALDI-TOF MS quantification of anthrax lethal toxin for diagnostics and evaluation of medical countermeasures", Anal Bioanal Chem, 407:2847-2858.

Kuklenyik Z, et al., (2011) "Comparison of MALDI-TOF-MS and HPLC-ESI-MS/MS for endopeptidase activity-based quantification of anthrax lethal factor in serum", Anal Chem. 83:1760-1765.

Turk BE, et al., (2004) "The structural basis for substrate and inhibitor selectivity of the anthrax lethal factor", Nature Struct Mol Biol, 11:60-66.

Tonello F, et al., (2002) "Screening inhibitors of anthrax lethal factor", Nature, 418:386.

Zkharova et al., (2009) "Substrate Recognition of Anthrax Lethal Factor Examined by Combinatorial and Pre-steady-state Kinetic Approaches" J. Biol. Chem, 284(27):17902-17913.

* cited by examiner

*Primary Examiner* — Mary Maille Lyons
(74) *Attorney, Agent, or Firm* — Carol L. Francis; Bozicevic, Field & Francis LLP

(57) ABSTRACT

Disclosed herein is a peptide substrate that is cleaved specifically by anthrax lethal factor (LF), and assays for detecting the presence of anthrax lethal factor in a sample using the peptide substrate. In some cases, the sample may be obtained from an individual at an early stage of an anthrax infection. Kits that include the peptide substrate and that find use in carrying out the assays are also disclosed.

24 Claims, 11 Drawing Sheets

Figure 11A

Lethal factor precursor [Bacillus anthracis]
GenBank: AAA79216.1; Gene ID: 3361711

```
  1 mnikkefikv ismsclvtai tlsgpvfipl vggagghgdv gmhvkekekn kdenkrkdee
 61 rnktqeehlk eimkhivkie vkgeeavkke aaekllekvp sdvlemykai ggkiyivdgd
121 itkhisleal sedkkkikdi ygkdallheh yvyakegyep vlviqssedy ventekalnv
181 yyeigkilsr dilskinqpy qkfidvlnti knasdsdgqd llftnqlkeh ptdfsvefie
241 qnsnevqevf akafayyiep qhrdvlqlya peafnymdkf neqeinlsie elkdqrmlsr
301 yekwekikqh yqhwsdslse egrgllkklq iplepkkddi ihsisqeeke ilkriqidss
361 dflsteekef ikklqidird slseeekell nriqvdssnp lsekekefik klkldiqpyd
421 inqrlqdtgg lidspsinld vrkqykrdiq nidallhqsi qstiynkiyl yenmninnit
481 atlgadlvds tdntkinrgi fnefkknfky sissnymivd inerpaldne rlkwriqlsp
541 dtragyleng klilqrnigl eikdvqiikq sekeyirida kvvpkskidt kiqeaqlnin
601 qewnkaiglp kytklitfnv hnryasnive sayiilnewk nniqsdlikk vtnylvdgng
661 rfvftditlp niaeqythqd eiyeqvhskq lyvpesrsil lhgpskqvel rndsegfihe
721 fghavddyag ylldknqsdl vtnskkfidi fkeegsnlts ygrtneaeff aeafrlmhst
781 dhaerlkvqk napktfqfin dqikfiins (SEQ ID NO:11)
```

The signal peptide at the N-terminus of the precursor is underlined. The signal peptide is cleaved by signal peptidases during secretion by B. anthracis, releasing the mature form of the protease (amino acids 34-809) into the environment.

Figure 11B

Protective antigen precursor [Bacillus anthracis]
GenBank: AAA22637.1; Gene ID: 3361714

```
  1 mkkrkvlipl malstilvss tgnleviqae vkqenrllne sesssqgllg yyfsdinfqa
 61 pmvvtssttg dlsipssele nipsenqyfq saiwsgfikv kksdeytfat sadnhvtmwv
121 ddqevinkas nsnkirlekg rlyqikiqyq renptekgld fklywtdsqn kkevissdnl
181 qlpelkqkss nsrkkrstsa qptvpdrdnd qipdsleveg ytvdvknkrt flspwisnih
241 ekkgltkyks spekwstasd pysdfekvtg ridknvspea rhplvaaypi vhvdmeniil
301 sknedqstqn tdsetrtisk ntstsrthts evhgnaevha sffdiqgsvs agfsnsnsst
361 vaidhslsla gertwaetmg lntadtarln aniryvntgt apiynvlptt slvlgknqtl
421 atikakenql sqilapnnyy pskniapial naqddfsstp itmnynqfle lektkqlrld
481 tdqvyqniat ynfengrvrv dtqsnwsevl pqiqettari ifngkdlnlv erriaavnps
541 dpletttkpdm tlkealkiaf gfnepngnlq yqgkditefd fnfdqqtsqn iknqlaelna
601 tniytvldki klnakmnili rdkrfhydrn niavgadesv vkeahrevin ssteqllini
661 dkdirkilsg yiveiedteg lkevindryd mlnisslrqd gktfidfkky ndklplyisn
721 pnykvnvyav tkentiinps engdtstngi kkilifskkg yeig (SEQ ID NO:12)
```

The furin cleavage site is underlined. Protective antigen 63 (PA63) is the C-terminal product (amino acids 197-764) of cleavage by furin at the furin cleavage site.

SEQUENCE LISTING

```
<160> NUMBER OF SEQ ID NOS: 12

<210> SEQ ID NO 1
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: This residue is covalently linked to
      7-methoxycoumarin-4-acetyl
<220> FEATURE:
<221> NAME/KEY: MISC_FEATURE
<222> LOCATION: (11)..(12)
<223> OTHER INFORMATION: A 2,4-dinitrophenol is covalently linked
      between these two residues.

<400> SEQUENCE: 1

Arg Arg Lys Lys Val Tyr Pro Tyr Pro Met Glu Thr Ile Ala
1               5                   10

<210> SEQ ID NO 2
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: This residue is covalently linked to 7-amido-
      4-methylcoumarin.

<400> SEQUENCE: 2

Arg Arg Lys Lys Val Tyr Pro
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: This residue is a D-isomer amino acid.
<220> FEATURE:
<221> NAME/KEY: MISC_FEATURE
<222> LOCATION: (3)..(3)
<223> OTHER INFORMATION: This residue is a D-isomer amino acid.
<220> FEATURE:
<221> NAME/KEY: MISC_FEATURE
<222> LOCATION: (4)..(4)
<223> OTHER INFORMATION: This residue is a D-isomer amino acid.
<220> FEATURE:
<221> NAME/KEY: MISC_FEATURE
<222> LOCATION: (7)..(7)
<223> OTHER INFORMATION: This residue is covalently linked to 7-amido-
      4-methylcoumarin.
```

```
<400> SEQUENCE: 3

Arg Arg Lys Lys Val Tyr Pro
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: This residue is a D-isomer amino acid.
<220> FEATURE:
<221> NAME/KEY: MISC_FEATURE
<222> LOCATION: (2)..(2)
<223> OTHER INFORMATION: This residue is a D-isomer amino acid.
<220> FEATURE:
<221> NAME/KEY: MISC_FEATURE
<222> LOCATION: (3)..(3)
<223> OTHER INFORMATION: This residue is a D-isomer amino acid.
<220> FEATURE:
<221> NAME/KEY: MISC_FEATURE
<222> LOCATION: (4)..(4)
<223> OTHER INFORMATION: This residue is a D-isomer amino acid.
<220> FEATURE:
<221> NAME/KEY: MISC_FEATURE
<222> LOCATION: (7)..(7)
<223> OTHER INFORMATION: This residue is covalently linked to 7-amido-
      4-methylcoumarin.

<400> SEQUENCE: 4

Arg Arg Lys Lys Val Tyr Pro
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: This residue is a D-isomer amino acid.
<220> FEATURE:
<221> NAME/KEY: MISC_FEATURE
<222> LOCATION: (2)..(2)
<223> OTHER INFORMATION: This residue is a D-isomer amino acid.
<220> FEATURE:
<221> NAME/KEY: MISC_FEATURE
<222> LOCATION: (5)..(5)
<223> OTHER INFORMATION: This residue is covalently linked to 7-amido-
      4-methylcoumarin.

<400> SEQUENCE: 5

Lys Lys Val Tyr Pro
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: This residue is a D-isomer amino acid.
<220> FEATURE:
<221> NAME/KEY: MISC_FEATURE
<222> LOCATION: (3)..(3)
```

```
<223> OTHER INFORMATION: This residue is a D-isomer amino acid.
<220> FEATURE:
<221> NAME/KEY: MISC_FEATURE
<222> LOCATION: (4)..(4)
<223> OTHER INFORMATION: This residue is a D-isomer amino acid.
<220> FEATURE:
<221> NAME/KEY: MISC_FEATURE
<222> LOCATION: (7)..(7)
<223> OTHER INFORMATION: This residue is covalently linked to
      7-amido-4-trifluoromethylcoumarin

<400> SEQUENCE: 6

Arg Arg Lys Lys Val Tyr Pro
1               5

<210> SEQ ID NO 7
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: This residue is a D-isomer amino acid.
<220> FEATURE:
<221> NAME/KEY: MISC_FEATURE
<222> LOCATION: (3)..(3)
<223> OTHER INFORMATION: This residue is a D-isomer amino acid.
<220> FEATURE:
<221> NAME/KEY: MISC_FEATURE
<222> LOCATION: (4)..(4)
<223> OTHER INFORMATION: This residue is a D-isomer amino acid.
<220> FEATURE:
<221> NAME/KEY: MISC_FEATURE
<222> LOCATION: (9)..(9)
<223> OTHER INFORMATION: This residue is a D-isomer amino acid.
<220> FEATURE:
<221> NAME/KEY: MISC_FEATURE
<222> LOCATION: (10)..(10)
<223> OTHER INFORMATION: This residue is a D-isomer amino acid.
<220> FEATURE:
<221> NAME/KEY: MISC_FEATURE
<222> LOCATION: (11)..(11)
<223> OTHER INFORMATION: This residue is a D-isomer amino acid.
<220> FEATURE:
<221> NAME/KEY: MISC_FEATURE
<222> LOCATION: (14)..(14)
<223> OTHER INFORMATION: This residue is covalently linked to rhodamine.

<400> SEQUENCE: 7

Arg Arg Lys Lys Val Tyr Pro Arg Arg Lys Lys Val Tyr Pro
1               5                   10

<210> SEQ ID NO 8
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: This residue may be either present or absent:
      when present, this amino acid may be any basic amino acid, any
      D-isomer basic amino acid, or any L-isomer basic amino acid.
<220> FEATURE:
<221> NAME/KEY: MISC_FEATURE
<222> LOCATION: (2)..(2)
<223> OTHER INFORMATION: This residue may be any basic amino acid, or
      any D-isomer basic amino acid.
<220> FEATURE:
<221> NAME/KEY: MISC_FEATURE
<222> LOCATION: (3)..(3)
<223> OTHER INFORMATION: This residue may be any basic amino acid, or
```

```
      any D-isomer basic amino acid.
<220> FEATURE:
<221> NAME/KEY: MISC_FEATURE
<222> LOCATION: (4)..(4)
<223> OTHER INFORMATION: This residue may be any basic amino acid, or
      any D-isomer basic amino acid.
<220> FEATURE:
<221> NAME/KEY: MISC_FEATURE
<222> LOCATION: (5)..(5)
<223> OTHER INFORMATION: This residue may be any amino acid, or any
      L-isomer amino acid.
<220> FEATURE:
<221> NAME/KEY: MISC_FEATURE
<222> LOCATION: (6)..(6)
<223> OTHER INFORMATION: This residue may be any hydrophobic or polar
      uncharged amino acid, or Tyr, or any L-isomer hydrophobic or polar
      uncharged amino acid, or L-Tyr.
<220> FEATURE:
<221> NAME/KEY: MISC_FEATURE
<222> LOCATION: (7)..(7)
<223> OTHER INFORMATION: This residue may be any amino acid, or any
      L-isomer amino acid; This residue is covalently linked to a
      moiety.

<400> SEQUENCE: 8

Xaa Xaa Xaa Xaa Xaa Xaa Xaa
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: This residue may be either present or absent:
      when present, this amino acid may be any basic amino acid, any
      D-isomer basic amino acid, or any L-isomer basic amino acid.
<220> FEATURE:
<221> NAME/KEY: MISC_FEATURE
<222> LOCATION: (2)..(2)
<223> OTHER INFORMATION: This residue may be any basic amino acid, or
      any D-isomer basic amino acid.
<220> FEATURE:
<221> NAME/KEY: MISC_FEATURE
<222> LOCATION: (3)..(3)
<223> OTHER INFORMATION: This residue may be any basic amino acid, or
      any D-isomer basic amino acid.
<220> FEATURE:
<221> NAME/KEY: MISC_FEATURE
<222> LOCATION: (4)..(4)
<223> OTHER INFORMATION: This residue may be any basic amino acid, or
      any D-isomer basic amino acid.
<220> FEATURE:
<221> NAME/KEY: MISC_FEATURE
<222> LOCATION: (5)..(5)
<223> OTHER INFORMATION: This residue may be any amino acid, or any
      L-isomer amino acid.
<220> FEATURE:
<221> NAME/KEY: MISC_FEATURE
<222> LOCATION: (6)..(6)
<223> OTHER INFORMATION: This residue may be any hydrophobic or polar
      uncharged amino acid, or Tyr, or any L-isomer hydrophobic or polar
      uncharged amino acid, or L-Tyr.

<400> SEQUENCE: 9

Xaa Xaa Xaa Xaa Xaa Xaa
1               5

<210> SEQ ID NO 10
<211> LENGTH: 7
<212> TYPE: PRT
<213> ORGANISM: Artificial sequence
```

-continued

```
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: This residue may be either present or absent:
      when present, this amino acid may be any basic amino acid, any
      D-isomer basic amino acid, or any L-isomer basic amino acid.
<220> FEATURE:
<221> NAME/KEY: MISC_FEATURE
<222> LOCATION: (2)..(2)
<223> OTHER INFORMATION: This residue may be any basic amino acid, or
      any D-isomer basic amino acid.
<220> FEATURE:
<221> NAME/KEY: MISC_FEATURE
<222> LOCATION: (3)..(3)
<223> OTHER INFORMATION: This residue may be any basic amino acid, or
      any D-isomer basic amino acid.
<220> FEATURE:
<221> NAME/KEY: MISC_FEATURE
<222> LOCATION: (4)..(4)
<223> OTHER INFORMATION: This residue may be any basic amino acid, or
      any D-isomer basic amino acid.
<220> FEATURE:
<221> NAME/KEY: MISC_FEATURE
<222> LOCATION: (5)..(5)
<223> OTHER INFORMATION: This residue may be any amino acid, or any
      L-isomer amino acid.
<220> FEATURE:
<221> NAME/KEY: MISC_FEATURE
<222> LOCATION: (6)..(6)
<223> OTHER INFORMATION: This residue may be any hydrophobic or polar
      uncharged amino acid, or Tyr, or any L-isomer hydrophobic or polar
      uncharged amino acid, or L-Tyr.
<220> FEATURE:
<221> NAME/KEY: MISC_FEATURE
<222> LOCATION: (7)..(7)
<223> OTHER INFORMATION: This residue may be any amino acid, or any
      L-isomer amino acid

<400> SEQUENCE: 10

Xaa Xaa Xaa Xaa Xaa Xaa Xaa
1               5

<210> SEQ ID NO 11
<211> LENGTH: 809
<212> TYPE: PRT
<213> ORGANISM: Bacillus anthracis

<400> SEQUENCE: 11

Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Glu Arg Asn Lys Thr
    50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140
```

```
Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
            165                 170                 175

Ala Leu Asn Val Tyr Tyr Glu Ile Gly Lys Ile Leu Ser Arg Asp Ile
        180                 185                 190

Leu Ser Lys Ile Asn Gln Pro Tyr Gln Lys Phe Leu Asp Val Leu Asn
    195                 200                 205

Thr Ile Lys Asn Ala Ser Asp Ser Asp Gly Gln Asp Leu Leu Phe Thr
210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

Tyr Ile Glu Pro Gln His Arg Asp Val Leu Gln Leu Tyr Ala Pro Glu
                260                 265                 270

Ala Phe Asn Tyr Met Asp Lys Phe Asn Glu Gln Glu Ile Asn Leu Ser
            275                 280                 285

Leu Glu Glu Leu Lys Asp Gln Arg Met Leu Ser Arg Tyr Glu Lys Trp
290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
                325                 330                 335

Lys Asp Asp Ile Ile His Ser Leu Ser Gln Glu Glu Lys Glu Leu Leu
                340                 345                 350

Lys Arg Ile Gln Ile Asp Ser Ser Asp Phe Leu Ser Thr Glu Glu Lys
            355                 360                 365

Glu Phe Leu Lys Lys Leu Gln Ile Asp Ile Arg Asp Ser Leu Ser Glu
        370                 375                 380

Glu Glu Lys Glu Leu Leu Asn Arg Ile Gln Val Asp Ser Ser Asn Pro
385                 390                 395                 400

Leu Ser Glu Lys Glu Lys Glu Phe Leu Lys Lys Leu Lys Leu Asp Ile
                405                 410                 415

Gln Pro Tyr Asp Ile Asn Gln Arg Leu Gln Asp Thr Gly Gly Leu Ile
                420                 425                 430

Asp Ser Pro Ser Ile Asn Leu Asp Val Arg Lys Gln Tyr Lys Arg Asp
            435                 440                 445

Ile Gln Asn Ile Asp Ala Leu Leu His Gln Ser Ile Gly Ser Thr Leu
    450                 455                 460

Tyr Asn Lys Ile Tyr Leu Tyr Glu Asn Met Asn Ile Asn Asn Leu Thr
465                 470                 475                 480

Ala Thr Leu Gly Ala Asp Leu Val Asp Ser Thr Asp Asn Thr Lys Ile
                485                 490                 495

Asn Arg Gly Ile Phe Asn Glu Phe Lys Lys Asn Phe Lys Tyr Ser Ile
            500                 505                 510

Ser Ser Asn Tyr Met Ile Val Asp Ile Asn Glu Arg Pro Ala Leu Asp
        515                 520                 525

Asn Glu Arg Leu Lys Trp Arg Ile Gln Leu Ser Pro Asp Thr Arg Ala
    530                 535                 540

Gly Tyr Leu Glu Asn Gly Lys Leu Ile Leu Gln Arg Asn Ile Gly Leu
545                 550                 555                 560
```

```
Glu Ile Lys Asp Val Gln Ile Ile Lys Gln Ser Lys Glu Tyr Ile
            565                 570                 575

Arg Ile Asp Ala Lys Val Val Pro Lys Ser Lys Ile Asp Thr Lys Ile
        580                 585                 590

Gln Glu Ala Gln Leu Asn Ile Asn Gln Glu Trp Asn Lys Ala Leu Gly
            595                 600                 605

Leu Pro Lys Tyr Thr Lys Leu Ile Thr Phe Asn Val His Asn Arg Tyr
        610                 615                 620

Ala Ser Asn Ile Val Glu Ser Ala Tyr Leu Ile Leu Asn Glu Trp Lys
625                 630                 635                 640

Asn Asn Ile Gln Ser Asp Leu Ile Lys Lys Val Thr Asn Tyr Leu Val
                645                 650                 655

Asp Gly Asn Gly Arg Phe Val Phe Thr Asp Ile Thr Leu Pro Asn Ile
            660                 665                 670

Ala Glu Gln Tyr Thr His Gln Asp Glu Ile Tyr Glu Gln Val His Ser
        675                 680                 685

Lys Gly Leu Tyr Val Pro Glu Ser Arg Ser Ile Leu Leu His Gly Pro
            690                 695                 700

Ser Lys Gly Val Glu Leu Arg Asn Asp Ser Glu Gly Phe Ile His Glu
705                 710                 715                 720

Phe Gly His Ala Val Asp Asp Tyr Ala Gly Tyr Leu Leu Asp Lys Asn
                725                 730                 735

Gln Ser Asp Leu Val Thr Asn Ser Lys Lys Phe Ile Asp Ile Phe Lys
            740                 745                 750

Glu Glu Gly Ser Asn Leu Thr Ser Tyr Gly Arg Thr Asn Glu Ala Glu
        755                 760                 765

Phe Phe Ala Glu Ala Phe Arg Leu Met His Ser Thr Asp His Ala Glu
    770                 775                 780

Arg Leu Lys Val Gln Lys Asn Ala Pro Lys Thr Phe Gln Phe Ile Asn
785                 790                 795                 800

Asp Gln Ile Lys Phe Ile Ile Asn Ser
            805

<210> SEQ ID NO 12
<211> LENGTH: 764
<212> TYPE: PRT
<213> ORGANISM: Bacillus anthracis

<400> SEQUENCE: 12

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125
```

```
Ala Ser Asn Ser Asn Lys Ile Arg Leu Glu Lys Gly Arg Leu Tyr Gln
            130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
290                 295                 300

Asp Gln Ser Thr Gln Asn Thr Asp Ser Glu Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
530                 535                 540
```

```
Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
                580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
        610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
                660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
        690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
                740                 745                 750

Ile Leu Ile Phe Ser Lys Lys Gly Tyr Glu Ile Gly
            755                 760
```

ANTHRAX LETHAL FACTOR SUBSTRATES AND METHODS OF USE THEREOF

CROSS-REFERENCE TO RELATED APPLICATION

This application claims priority benefit to U.S. provisional application Ser. No. 62/245,736, filed Oct. 23, 2015, which application is incorporated herein by referenced in its entirety.

INTRODUCTION

*Bacillus anthracis* is the etiological agent of anthrax. The principal virulence factors are a γ-linked poly-D-glutamic acid (PGA) capsule and a three component exotoxin composed of protective antigen (PA), lethal factor (LF) and edema factor (EF). These proteins act in binary combinations. The complex of PA, the cell binding component, with the LF enzyme, is termed lethal toxin and can cause death. PA and the enzymatic EF together cause skin edema. Secreted PA is cleaved by membrane peptidases. This allows the 63 kDa carboxy terminal fragment to oligomerize to a heptamer or higher. Cleavage of PA exposes the binding sites for EF and LF. The complex enters the cell through endocytosis. PA mediates the transfer of LF and EF to the cytoplasm where these enzymes recognize and alter their targets.

There are three forms of human anthrax: cutaneous, inhalation, and gastrointestinal. About 95% of anthrax cases are cutaneous which are readily diagnosed and respond well to antimicrobial therapy. With the inhalational anthrax incident which resulted from the intentional release of anthrax spores in the bioterrorism attacks of 2001, early symptoms were similar to those for common illnesses. Once symptoms are severe and diagnosis is possible, the levels of toxins are dangerously high. The incubation period can vary from hours to weeks depending on the dose received. Once intoxication occurs, anthrax bacteria can multiply rapidly in the blood and begin to secrete significant quantities of the toxin. Thus, anthrax lethal factor-specific substrates, useful for early detection of lethal factor and early diagnosis of an anthrax infection, are of interest.

SUMMARY

Disclosed herein are peptide substrates that are cleaved specifically by anthrax lethal factor (LF), and assays for detecting the presence of anthrax lethal factor in a sample using the peptide substrate. A peptide substrate of the present disclosure may include an amino acid sequence of the formula $X^1-X^2-X^3-X^4-X^5-X^6-X^{7*}$ (SEQ ID NO:8), wherein $X^1$ is either present or absent, and when present, is Arg; $X^2$, $X^3$, $X^4$ are each independently selected from Lys and Arg; $X^5$ is selected from Gly and Val; $X^6$ is selected from Tyr, Leu, Ile, Thr and Asn; and $X^{7*}$ has the formula $X^7$—Z, where $X^7$ is Pro, and Z is a detectable label covalently linked by an amide linkage or an ester linkage to an alpha carboxyl group of $X^7$, and wherein at least one of $X^1$, $X^2$, $X^3$ and $X^4$, is a D isomer of the amino acid.

An anthrax lethal factor-specific peptide substrate containing an amino acid sequence of the formula $X^1-X^2-X^3-X^4-X^5-X^6-X^{7*}$ (SEQ ID NO:8), wherein $X^1$ is either present or absent, and when present, is Arg; $X^2$, $X^3$, $X^4$ are each independently selected from Lys and Arg; $X^5$ is selected from Gly and Val; $X^6$ is selected from Tyr, Leu, Ile, Thr and Asn; and $X^{7*}$ has the formula $X^7$—Z, where $X^7$ is Pro, and Z is a detectable label covalently linked by an amide linkage or an ester linkage to an alpha carboxyl group of $X^7$, and wherein at least one of $X^1$, $X^2$, $X^3$ and $X^4$, is a D isomer of the amino acid. In some embodiments, $X^5$ is Val. In some embodiments, $X^6$ is Tyr. In certain embodiments, $X^2$ is Arg; $X^3$ is Lys, and $X^4$ is Lys. In some embodiments, at least three of $X^1$, $X^2$, $X^3$ and $X^4$, are a D isomer of the amino acid. In certain cases, $X^2$ is D-Arg; $X^3$ is D-Lys; and $X^4$ is D-Lys. In some embodiments, $X^1$ is present and is D-Arg.

In any embodiment, the number of amino acids in the substrate may be less than 9.

In any embodiment, detection of the detectable label may specifically indicate cleavage of the linkage between $X^7$ and Z.

In any embodiment, the detectable label may include a coumarin, a rhodamine, or an aromatic dye. In some cases, the detectable label is 7-amido-4-methylcoumarin, 7-amido-4-trifluoromethylcoumarin, 7-amido-4-carbamoylmethylcoumarin, p-nitroanilide, or p-nitrophenyl ester.

Also disclosed herein is a method of producing the present peptide substrate using solid phase synthesis. In some cases, the method includes using solid phase synthesis to synthesize a peptide intermediate comprising an amino acid sequence of the formula $X^1-X^2-X^3-X^4-X^5-X^6$ (SEQ ID NO:9); and covalently attaching the carboxyl terminus of $X^6$ of the peptide intermediate to an amine group on the alpha carboxyl group of $X^{7*}$. In some cases, the method includes using solid phase synthesis to synthesize a peptide intermediate comprising an amino acid sequence of the formula $X^1-X^2-X^3-X^4-X^5-X^6-X^7$ (SEQ ID NO: 10); and covalently attaching the detectable label to the carboxyl terminus of the peptide intermediate. In certain embodiments, the method includes using solid phase synthesis to synthesize a peptide comprising an amino acid sequence of the formula $X^1-X^2-X^3-X^4-X^5-X^6-X^{7*}$ (SEQ ID NO: 8).

Also disclosed herein is a method of detecting anthrax lethal factor in a biological sample, including i) contacting a test sample derived from the biological sample with the anthrax lethal factor-specific peptide substrate as described herein, under conditions sufficient for anthrax lethal factor to cleave the substrate and generate a cleaved product, wherein the test sample comprises an assay buffer; and ii) measuring a level of the cleaved product in the test sample at one or more time points, wherein, anthrax lethal factor is determined to be present in the biological sample based on the measured level of the cleaved product at the one or more time points. In some cases, the test sample includes plasma or serum in the range of 5% to 30%. In some cases, the test sample is enriched for anthrax lethal factor. In some cases, the method further includes enriching for anthrax lethal factor in the biological sample by contacting the biological sample with an anthrax lethal factor-specific binding partner bound to a solid support, wherein the anthrax lethal factor-specific binding partner is configured to bind anthrax lethal factor, thereby generating a test sample enriched for anthrax lethal factor. In some cases, the anthrax lethal factor-specific binding partner includes a lethal factor-specific antibody or anthrax protective antigen 63 (PA63). In certain embodiments, the solid support is a bead, a column or a multi-well plate.

In any embodiment, the assay buffer may be a peptide substrate-specific assay buffer.

In any embodiment, the measuring may include using fluorescence spectroscopy, high-pressure liquid chromatography and/or mass spectrometry.

In any embodiment, the biological sample may include blood, plasma or serum.

In any embodiment, the anthrax lethal factor may be determined to be present in the biological sample when the measured level of the cleaved product at a time point is above a reference level. In some cases, the reference level is obtained from a reference sample that does not contain anthrax lethal factor.

In any embodiment, the measuring includes measuring a level of the cleaved product in the test sample at a plurality of time points, wherein the amount of anthrax lethal factor in the sample is determined based on the rate of change in the level of the cleaved product in the sample over the plurality of time points.

In any embodiment, the plurality of time points may be taken over 24 hours or less.

Also provided herein is a kit for detecting anthrax lethal factor in a biological sample. The kit may contain an anthrax lethal factor-specific peptide substrate of claim 1; and a standardization element. In some cases, the standardization element includes one or more positive reference samples, each comprising a known amount of anthrax lethal factor. In some cases, the standardization element includes a negative reference sample that does not comprise anthrax lethal factor. In some cases, the standardization element includes a standardization chart or table for converting one or more measured levels of a cleavage product of the peptide substrate to a concentration of lethal factor.

BRIEF DESCRIPTION OF THE DRAWINGS

FIGS. 11A and 11B show amino acid sequences of Bacillus anthracis lethal factor precursor and protective antigen precursor, respectively, according to embodiments of the present disclosure.

DEFINITIONS

Figure 1:
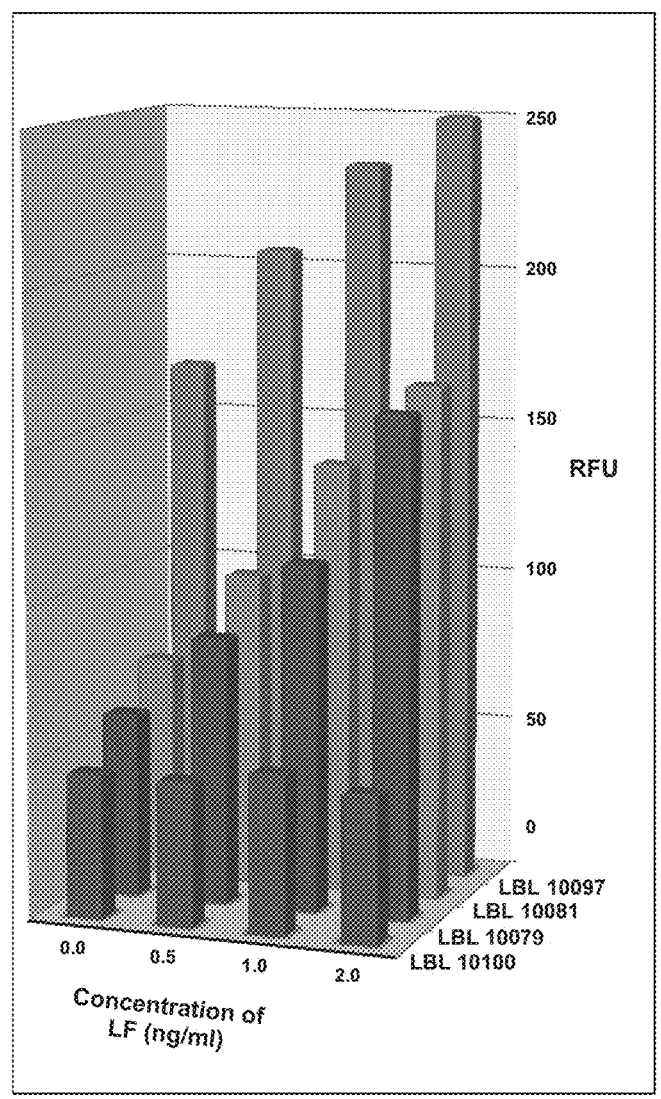
FIG. 1 is a graph showing measured fluorescence from lethal factor (LF)-specific peptide substrates cleaved by LF in buffer, according to embodiments of the present disclosure.

The terms "polypeptide", "peptide" and "protein" are used interchangeably herein to refer to polymers of amino acids of any length. The polymer may be linear, it may comprise modified amino acids, it may be interrupted by non-amino acids, and all or part of the backbone of the polymer may be replaced with non-naturally occurring or synthetic backbones, e.g., contain amide bond isosteres. The terms also encompass an amino acid polymer that has been modified; for example, by disulfide bond formation, glycosylation, lipidation, acetylation, phosphorylation, or any other modification, such as conjugation with a labeling component.

As used herein the term "amino acid" refers to naturally occurring amino acids, including D and L isomers, and amino acid analogs, unless indicated otherwise. The terms "amino acid analog" include amino acid-like compounds that are similar in structure and/or overall shape to one or more amino acids commonly found in naturally occurring proteins. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof.

The "alpha carboxyl group" of an amino acid refers to the carbon atom of the alpha carboxylic acid or carboxylate group attached directly to the alpha carbon atom of the amino acid residue. In a generic formula of an amino acid: $H_2NCHRCOOH$, where R is a side chain, the alpha carbon is the first carbon in the formula, and the alpha carboxyl carbon is the last carbon in the formula. The alpha carboxyl group in an amino acid residue that is part of the present peptide substrate may refer to the carbonyl carbon attached directly to the alpha carbon of an amino acid residue, where the amino acid residue has a peptide linkage or an ester linkage to a detectable label.

It will be appreciated that throughout the present disclosure reference is made to amino acids according to the single letter or three letter codes. For the reader's convenience, the single and three letter amino acid codes are provided below. In addition, the amino acid residues provided below are divided into categories based on their chemical properties. The headings provided in the table below (Nonpolar, Hydrophobic; Polar, Uncharged; Polar, Acidic; and Polar, Basic) are used to refer generally to amino acid residues with side chains having the identified chemical properties.

| Nonpolar, Hydrophobic Residues | | |
|---|---|---|
| Alanine | Ala | A |
| Valine | Val | V |
| Leucine | Leu | L |
| Isoleucine | Ile | I |

-continued

| Nonpolar, Hydrophobic Residues | | |
|---|---|---|
| Polar, Acidic | | |
| Aspartic Acid | Asp | D |
| Glutamic Acid | Glu | E |
| Polar, Uncharged Residues | | |
| Glycine | Gly | G |
| Serine | Ser | S |
| Threonine | Thr | T |
| Cysteine | Cys | C |
| Nonpolar, Hydrophobic Residues | | |
| Phenylalanine | Phe | F |
| Tryptophan | Trp | W |
| Methionine | Met | M |
| Proline | Pro | P |
| Nonpolar, Hydrophobic Residues | | |
| Tyrosine | Tyr | Y |
| Asparagine | Asn | N |
| Glutamine | Gln | Q |
| Polar, Basic | | |
| Lysine | Lys | K |
| Arginine | Arg | R |
| Histidine | His | H |

As used herein in the context of the structure of a polypeptide, "amino terminus" or "N-terminus" refers to the terminal amino acid residues having a free amino group, which amine group in non-N-terminus amino acid residues normally forms part of the covalent backbone of the polypeptide. "Carboxyl terminus" or "C-terminus" refers to the terminal amino acid residues having a free carboxyl group, which carboxyl group in non-C-terminus amino acid residues normally forms part of the covalent backbone of the polypeptide. "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

By "antibody" is meant a protein of one or more polypeptides that specifically binds an antigen and that are substantially encoded by all or part of the recognized immunoglobulin genes. The recognized immunoglobulin genes, for example in humans, include the kappa (κ), lambda (λ), and heavy chain genetic loci, which together contain the myriad variable region genes, and the constant region genes mu (μ), delta (δ), gamma (γ), sigma (σ), and alpha (α) which encode the IgM, IgD, IgG, IgE, and IgA antibody "isotypes" or "classes" respectively. Antibody herein is meant to include full length antibodies and antibody fragments, and may refer to a natural antibody from any organism, an engineered antibody, or an antibody generated recombinantly for experimental, therapeutic, or other purposes. The term "antibody" includes full length antibodies, and antibody fragments, as are known in the art, such as Fab, Fab', F(ab')$_2$, Fv, scFv, or other antigen-binding subsequences of antibodies, either produced by the modification of whole antibodies or those synthesized de novo using recombinant DNA technologies. Methods for generating antibodies that bind specifically to a target protein or antigen of interest are known.

"Substantially" as used herein, may be applied to modify any quantitative representation that could permissibly vary without resulting in a change in the basic function to which it is related. For example, an antibody that binds LF may permissively have a somewhat inhibitory effect on the LF catalytic activity, if the sensitivity of the subsequent LF detection assay using the LF purified by the antibody is not materially altered.

The term "binding" refers to a direct association between two molecules, due to, for example, covalent, electrostatic, hydrophobic, and ionic and/or hydrogen-bond interactions, including interactions such as salt bridges and water bridges. An LF-specific binding partner binds specifically to an epitope within an LF protein. "Specific binding" refers to a preferential binding interaction between a first and second member of a specific binding partner over interaction between the first or second member and a third member that may or may not have a binding interaction with the first or second member.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polypeptides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

A "detectable label" includes any moiety that can be detected by measuring a signal specific to the moiety. The signal specific to the moiety may be absorption and/or emission of electromagnetic radiation of a specific wavelength, a unique mass, etc. A detectable label may be a moiety that includes a radioisotope, fluorogenic or chromogenic moiety, etc. A fluorogenic or chromogenic moiety includes fluorophores or chromophores that can be detected using colorimetric or fluorometric methods.

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a peptide substrate" includes a plurality of such peptide substrates and reference to "the binding partner" includes reference to one or more binding partners and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication by virtue of prior invention. Further, the dates of publication provided may be different from the actual publication dates which may need to be independently confirmed.

DETAILED DESCRIPTION

As summarized above, the present disclosure includes a peptide substrate that is cleaved specifically by *Bacillus anthracis* lethal factor (also referred to herein as anthrax LF, or LF). The peptide substrate may include an amino acid sequence of the formula $X^1$-$X^2$-$X^3$-$X^4$-$X^5$-$X^6$-$X^{7*}$ (SEQ ID NO:8), wherein $X^1$ is either present or absent, and when present, is Arg; $X^2$, $X^3$, $X^4$ are each independently selected from Lys and Arg; $X^5$ is selected from Gly and Val; $X^6$ is selected from Tyr, Leu, Ile, Thr and Asn; and $X^{7*}$ has the formula $X^7$—Z, where $X^7$ is Pro, and Z is a detectable label covalently linked by an amide linkage or an ester linkage to an alpha carboxyl group of $X^7$, and wherein at least one of $X^1$, $X^2$, $X^3$ and $X^4$, is a D isomer of the amino acid. Further aspects of the present peptide substrate are now described.

Peptide Substrates

The peptide substrate of the present disclosure includes an amino acid sequence covalently linked to a detectable label, where the peptide substrate can be recognized by anthrax LF and be cleaved to yield a cleavage product. The amino acid sequence of anthrax LF is shown in FIG. 11A. When the present peptide substrate is contacted with a sample containing LF, the level of the cleavage product provides an indication of the amount of catalytically active anthrax LF in a sample. In some cases, the cleavage product includes the detectable label.

The present peptide substrate is specific to anthrax LF, such that when the peptide substrate is contacted with a sample, such as a sample derived from blood, plasma or serum, that contains LF, the peptide substrate is cleaved to yield a detectable LF protease activity-specific cleavage product. In the absence of LF, the LF-specific peptide substrate does not yield a detectable LF protease activity-specific cleavage product, even if the sample may contain other non-LF proteases commonly found in the sample source, e.g., blood, plasma, serum, etc. Thus, in some cases, where the peptide substrate contains a detectable label, as further described below, the label is undetectable over background when contacted with a sample, such as a sample derived from blood, plasma, or serum, that does not contain LF, but that may contain other non-LF proteases commonly found in blood, plasma or serum. As such, detection of cleavage products of the anthrax LF-specific peptide substrate provides an indication that the peptide substrate was cleaved by LF protease activity and not by non-specific protease activity in the sample.

The present peptide substrate may contain an amino acid sequence of any suitable length for the peptide substrate to serve as a LF-specific substrate and yield a LF-specific cleavage product. The peptide substrate may include an amino acid sequence that is 6 or more, e.g., 7 or more, 8 or more, 9 or more, 10 or more, 15 or more, 20 or more, 30 or more, 40 or more, 50 or more, 75 or more, including 100 or more amino acids long, and may be 1000 or fewer, e.g., 750 or fewer, 500 or fewer, 250 or fewer, 100 or fewer, 50 or fewer, 30 or fewer, 20 or fewer, 11 or fewer, 10 or fewer, 9 or fewer, including 8 or fewer amino acids long. In some cases, peptide substrate includes an amino acid sequence having a length in the range of 6 to 500, e.g., 6 to 100, 6 to 50, 6 to 20, 6 to 11, including 7 to 10 amino acids.

The peptide substrate of the present disclosure includes an amino acid sequence represented by the formula: $X^1$-$X^2$-$X^3$-$X^4$-$X^5$-$X^6$-$X^{7*}$ (SEQ ID NO:8), wherein $X^1$ may be either present or absent, and when present may be a basic amino acid; $X^2$, $X^3$, $X^4$ may each independently be a basic amino acid; $X^5$ may be any amino acid; $X^6$ may be a hydrophobic or polar, uncharged amino acid; and $X^{7*}$ has the formula $X^7$—Z, where $X^7$ is Pro, and Z is a moiety covalently linked by an amide linkage or an ester linkage to an alpha carboxyl group of $X^7$, wherein Z is selected from a detectable label or a polypeptide, and wherein at least one, e.g., at least two, at least three, or all four, of $X^1$, $X^2$, $X^3$, and $X^4$, are a D isomer of the amino acid.

The present peptide substrate is a specific substrate for LF, which cleaves the peptide substrate at the covalent linkage between $X^7$ and Z. Thus, the covalent bond between $X^7$ and Z is an amide or ester bond that can be hydrolyzed by LF when the peptide substrate is contacted with LF. In other words, the cleavage site for LF in the peptide substrate is between $X^7$ and Z.

In some cases, Z is a detectable label. The detectable label may be any suitable detectable label, as described in detail below. In certain cases, the detectable label is a fluorogenic label or a chromogenic label. In some cases, the detectable label is a coumarin, or derivative thereof, a rhodamine, or derivative thereof, or an aromatic dye. In some cases, the detectable label is 7-amido-4-methylcoumarin, 7-amido-4-trifluoromethylcoumarin, 7-amido-4-carbamoylmethylcoumarin, p-nitroanilide, or p-nitrophenyl ester.

In some cases, Z is a polypeptide. The polypeptide may be any suitable polypeptide for use in the present LF-specific peptide substrate. In some cases, the polypeptide includes an amino acid sequence having a length of 1 to 100, e.g., 1 to 50, 1 to 30, 1 to 20, including 1 to 15 amino acids. The polypeptide may include any suitable amino acid sequence that provides an indication for LF-specific cleavage of the peptide substrate between $X^7$ and Z.

In some embodiments, a peptide substrate of the present disclosure includes the amino acid sequence $X^1$-$X^2$-$X^3$-$X^4$-$X^5$-$X^6$-$X^{7*}$ (SEQ ID NO:8), wherein $X^1$ may be either present or absent, and when present may be selected from Lys and Arg; $X^2$, $X^3$, $X^4$ may each be independently selected from Lys and Arg; $X^5$ may be any amino acid; $X^6$ may be selected from Tyr, Leu, Ile, Thr and Asn; and $X^{7*}$ has the formula $X^7$—Z, where $X^7$ is Pro, and Z is a moiety covalently linked by an amide linkage or an ester linkage to an alpha carboxyl group of $X^7$, wherein Z is selected from a detectable label or a polypeptide comprising an amino acid sequence having a length of 1 to 20 amino acids, and wherein at least one, e.g., at least two, at least three, or all four, of $X^1$, $X^2$, $X^3$, and $X^4$, are a D isomer of the amino acid. In some embodiments, $X^5$ is Val. In some cases, $X^6$ is Tyr. In certain embodiments, $X^1$, if present, is Arg; $X^2$ is Arg; $X^3$ is Lys, and $X^4$ is Lys. In some cases, the peptide substrate contains 11 or less, e.g., 10 or less, 9 or less, including 8 or less amino acids. In some cases, Z is a detectable label. The detectable label may be any suitable detectable label, as described below. In certain cases, the detectable label is a fluorogenic label or a chromogenic label. In some cases, the detectable label includes a coumarin, a rhodamine or an aromatic dye. In some cases, the detectable label is 7-amido-4-methylcoumarin, 7-amido-4-trifluoromethylcoumarin, 7-amido-4-carbamoylmethylcoumarin, p-nitroanilide, or p-nitrophenyl ester.

In some embodiments, a peptide substrate of the present disclosure includes the amino acid sequence $X^1$-$X^2$-$X^3$-$X^4$-$X^5$-$X^6$-$X^{7*}$ (SEQ ID NO:8), wherein $X^1$ is either present or absent, and when present is Arg; $X^2$, $X^3$, $X^4$ are each independently selected from Lys and Arg; $X^5$ is selected from Gly and Val; $X^6$ is selected from Tyr, Leu, Ile, Thr and Asn; and $X^{7*}$ has the formula $X^7$—Z, where $X^7$ is Pro, and Z is a moiety covalently linked by an amide linkage or an ester linkage to an alpha carboxyl group of $X^7$, wherein Z is a detectable label, and wherein at least three of $X^1$, $X^2$, $X^3$, and $X^4$, are a D isomer of the amino acid. In some embodiments, $X^5$ is Val. In some cases, $X^6$ is Tyr. In certain embodiments, $X^2$ is Arg, $X^3$ is Lys, and $X^4$ is Lys. In some cases, the peptide substrate contains 11 or less, e.g., 10 or less, 9 or less, including 8 or less amino acids. The detectable label may be any suitable detectable label, as described below. In certain cases, the detectable label is a fluorogenic label or a chromogenic label. In some cases, the detectable label includes a coumarin, a rhodamine or an aromatic dye. In some cases, the detectable label is 7-amido-4-methylcoumarin, 7-amido-4-trifluoromethylcoumarin, 7-amido-4-carbamoylmethylcoumarin, p-nitroanilide, or p-nitrophenyl ester.

In some embodiments, a peptide substrate of the present disclosure includes the amino acid sequence $X^1$-$X^2$-$X^3$-$X^4$-$X^5$-$X^6$-$X^{7*}$ (SEQ ID NO:8), wherein $X^1$ is either present or absent, and when present is Arg; $X^2$, $X^3$, $X^4$ are each independently selected from Lys and Arg; $X^5$ is selected from L-Gly and L-Val; $X^6$ is selected from L-Tyr, L-Leu, L-Ile, L-Thr and L-Asn, and $X^{7*}$ has the formula $X^7$—Z, where $X^7$ is L-Pro, and Z is a moiety covalently linked by an amide linkage or an ester linkage to an alpha carboxyl group of $X^7$, wherein Z is a detectable label, and wherein at least one, e.g., at least two, at least three, or all four, of $X^1$, $X^2$, $X^3$, and $X^4$, are a D isomer of the amino acid. In some embodiments, $X^5$ is L-Val. In some cases, $X^6$ is L-Tyr. In certain embodiments, $X^2$ is Arg; $X^3$ is Lys, and $X^4$ is Lys. In some cases, the peptide substrate contains 11 or less, e.g., 10 or less, 9 or less, including 8 or less amino acids. In some cases, Z is a detectable label. The detectable label may be any suitable detectable label, as described below. In certain cases, the detectable label is a fluorogenic label or a chromogenic label. In some cases, the detectable label includes a coumarin, a rhodamine or an aromatic dye. In some cases, the detectable label is 7-amido-4-methylcoumarin, 7-amido-4-trifluoromethylcoumarin, 7-amido-4-carbamoylmethylcoumarin, p-nitroanilide, or p-nitrophenyl ester.

In some embodiments, a peptide substrate of the present disclosure includes the amino acid sequence $X^1$-$X^2$-$X^3$-$X^4$-$X^5$-$X^6$-$X^{7*}$ (SEQ ID NO:8), wherein $X^1$ is either present or absent, and when present is Arg; $X^2$ is Arg; $X^3$ is Lys, $X^4$ is Lys, $X^5$ is L-Val, $X^6$ is L-Tyr, and $X^{7*}$ has the formula $X^7$—Z, where $X^7$ is L-Pro, and Z is a moiety covalently linked by an amide linkage or an ester linkage to an alpha carboxyl group of L-Pro at $X^7$, wherein Z is a detectable label, and wherein at least one, e.g., at least two, at least three, or all four, of $X^1$, $X^2$, $X^3$, and $X^4$, are a D isomer of the amino acid. In some cases, the peptide substrate contains 11 or less, e.g., 10 or less, 9 or less, including 8 or less amino acids. The detectable label may be any suitable detectable label, as described below. In certain cases, the detectable label is a fluorogenic label or a chromogenic label. In some cases, the detectable label includes a coumarin, a rhodamine or an aromatic dye. In some cases, the detectable label is 7-amido-4-methylcoumarin, 7-amido-4-trifluoromethylcoumarin, 7-amido-4-carbamoylmethylcoumarin, p-nitroanilide, or p-nitrophenyl ester.

In some embodiments, a peptide substrate of the present disclosure includes the amino acid sequence $X^1$-$X^2$-$X^3$-$X^4$-$X^5$-$X^6$-$X^{7*}$ (SEQ ID NO:8), wherein $X^1$ is L-Arg; $X^2$ is D-Arg; $X^3$ is D-Lys, $X^4$ is D-Lys, $X^5$ is L-Val, $X^6$ is L-Tyr, and $X^{7*}$ has the formula $X^7$—Z, where $X^7$ is L-Pro, and Z is a moiety covalently linked by an amide linkage or an ester linkage to an alpha carboxyl group of L-Pro at $X^7$, wherein Z is a detectable label. In some cases, the peptide substrate contains 11 or less, e.g., 10 or less, 9 or less, including 8 or less amino acids. The detectable label may be any suitable detectable label, as described below. In certain cases, the detectable label is a fluorogenic label or a chromogenic label. In some cases, the detectable label includes a coumarin, a rhodamine or an aromatic dye. In some cases, the detectable label is 7-amido-4-methylcoumarin, 7-amido-4-trifluoromethylcoumarin, 7-amido-4-carbamoylmethylcoumarin, p-nitroanilide, or p-nitrophenyl ester. In some cases, the peptide substrate includes the amino acid sequence set forth in SEQ ID NOs:3, 6 or 7.

In some embodiments, a peptide substrate of the present disclosure includes the amino acid sequence $X^1$-$X^2$-$X^3$-$X^4$-$X^5$-$X^6$-$X^{7*}$ (SEQ ID NO:8), wherein $X^1$ is D-Arg; $X^2$ is D-Arg; $X^3$ is D-Lys, $X^4$ is D-Lys, $X^5$ is L-Val, $X^6$ is L-Tyr, and $X^{7*}$ has the formula $X^7$—Z, where $X^7$ is L-Pro, and Z is a moiety covalently linked by an amide linkage or an ester linkage to an alpha carboxyl group of L-Pro at $X^7$, wherein Z is a detectable label. In some cases, the peptide substrate contains 11 or less, e.g., 10 or less, 9 or less, including 8 or less amino acids. The detectable label may be any suitable detectable label, as described below. In certain cases, the detectable label is a fluorogenic label or a chromogenic label. In some cases, the detectable label includes a coumarin, a rhodamine or an aromatic dye. In some cases, the detectable label is 7-amido-4-methylcoumarin, 7-amido-4-trifluoromethylcoumarin, 7-amido-4-carbamoylmethylcoumarin, p-nitroanilide, or p-nitrophenyl ester. In some cases, the peptide substrate includes the amino acid sequence set forth in SEQ ID NO:4.

In some embodiments, a peptide substrate of the present disclosure includes the amino acid sequence $X^1$-$X^2$-$X^3$-$X^4$-$X^5$-$X^6$-$X^{7*}$ (SEQ ID NO:8), wherein $X^1$ is absent, $X^2$ is D-Arg; $X^3$ is D-Lys, $X^4$ is D-Lys, $X^5$ is L-Val, $X^6$ is L-Tyr, and $X^{7*}$ has the formula $X^7$—Z, where $X^7$ is L-Pro, and Z is a moiety covalently linked by an amide linkage or an ester linkage to an alpha carboxyl group of L-Pro at $X^7$, wherein Z is a detectable label. In some cases, the peptide substrate contains 11 or less, e.g., 10 or less, 9 or less, including 8 or less amino acids. The detectable label may be any suitable detectable label, as described below. In certain cases, the detectable label is a fluorogenic label or a chromogenic label. In some cases, the detectable label includes a coumarin, a rhodamine or an aromatic dye. In some cases, the detectable label is 7-amido-4-methylcoumarin, 7-amido-4-trifluoromethylcoumarin, 7-amido-4-carbamoylmethylcoumarin, p-nitroanilide, or p-nitrophenyl ester.

In some cases, the peptide substrate of the present disclosure is an inhibitory peptide that reduces or inhibits the protease activity of LF. A LF inhibitory peptide may include an amino acid sequence represented by the formula: $X^1$-$X^2$-$X^3$-$X^4$-$X^5$-$X^6$-$X^{7*}$ (SEQ ID NO:8), wherein $X^1$ is either present or absent, and when present is a basic amino acid; $X^2$, $X^3$, $X^4$ are each independently selected from a basic amino acid; $X^5$ is any amino acid; $X^6$ is a hydrophobic or polar, uncharged amino acid, and $X^{7*}$ has the formula $X^7$—Z, where $X^7$ is any amino acid, and Z is a moiety covalently to $X^7$, wherein Z is an inhibitory moiety, and wherein at least one, e.g., at least two, at least three, or all four, of $X^1$, $X^2$, $X^3$, and $X^4$, are a D isomer of the amino acid. The inhibitory moiety may be any suitable inhibitory moiety, such as, but not limited to, a hydroxamate (—NH—OH), or a derivative thereof. In some cases, the inhibitory moiety is N, O-dimethyl hydroxamate (—N($CH_3$)—O—$CH_3$).

Detectable Labels

As described above, the LF-specific peptide substrate of the present disclosure may include a detectable label. Any suitable detectable label that can be covalently linked to an alpha carboxyl group of a C-terminal amino acid of a peptide molecule via a peptide or an ester linkage may be used. The detectable label also will not significantly inhibit the ability of LF to cleave the peptide or ester bond linking (e.g., directly linking) the detectable label to the rest of the peptide substrate, if the peptide substrate is to be used to detect cleavage activity of LF in a sample.

Examples of suitable detectable labels include, but are not limited to, fluorescent molecules (e.g., autofluorescent molecules, molecules that fluoresce upon contact with a reagent, etc.), radioactive labels (e.g., $^{111}$In, $^{125}$I, $^{131}$I, $^{212}$B, $^{90}$Y, $^{186}$Rh, and the like), mass tags (e.g., lanthanide metals, or a polymer containing a lanthanide, etc., as described in PCT Pub. No. WO 2015038784, which is incorporated herein by reference), members of a binding pair (e.g., biotin, to be detected through reaction of biotin and avidin), fluorescent tags, imaging reagents, pH modulating agents, and the like. Detectable labels also include peptides or polypeptides that can be detected by antibody binding, e.g., by binding of a detectably labeled antibody or by detection of bound antibody through a sandwich-type assay. Further examples of detectable labels include, but are not limited to, dye labels (e.g., chromophores, fluorophores, such as, but not limited to, Alexa Fluor® fluorescent dyes (e.g., Alexa Fluor® 350, 405, 430, 488, 532, 546, 555, 568, 594, 595, 610, 633, 635, 647, 660, 680, 700, 750, 790, and the like)), biophysical probes (spin labels, nuclear magnetic resonance (NMR) probes), Förster Resonance Energy Transfer (FRET)-type labels (e.g., at least one member of a FRET pair, including at least one member of a fluorophore/quencher pair), Bioluminescence Resonance Energy Transfer (BRET)-type labels (e.g., at least one member of a BRET pair), tags (e.g., FLAG, His(6), and the like), localization tags (e.g., to identify association of a tagged polypeptide at the tissue or molecular cell level (e.g., association with a tissue type, or particular cell membrane), and the like.

Where the detectable label includes a member of a binding pair, a member of any suitable binding pair may be used. Suitable members of a binding pair include, without limitation, biotin, avidin, horseradish peroxidase, streptavidin, and digoxigenin.

In some cases, the detectable label is a chromophore, which may be any compound capable of being detected colorimetrically or fluorometrically. The detectable label may be any suitable chromophore that can be covalently linked to an alpha carboxyl group of a C-terminal amino acid of a peptide molecule via a peptide or an ester linkage. The specific examples disclosed herein describe chromophores detected by fluorescence. It should be understood, however, that the compounds and methods described can equally be utilized with chromophores that are detected by other means readily available to those skilled in the art, such as, for example, absorbance or phosphorescence.

In some cases, the chromophore is chromogenic, i.e. is detectable when the peptide substrate is specifically cleaved at the amide or ester bond linking (e.g., directly linking) the chromophore to the rest of the substrate. In such cases, a chromogenic label may be detectable by having different photospectral properties when the chromophore is covalently linked to the peptide substrate compared to when the chromophore is cleaved from the rest of the peptide substrate (i.e., cleaved from the C-terminal amino acid of the peptide substrate). In some cases, the chromogenic label is substantially not detectable by colorimetric or fluorometric methods when the chromogenic label is covalently bonded to the peptide substrate, but becomes detectable by the colorimetric or fluorometric methods when cleaved from the rest of the peptide substrate (i.e., cleaved from the C-terminal amino acid of the peptide substrate).

Chromophores of interest include fluorescent dye moieties. The fluorescent dye moiety may be a fluorogenic dye that fluoresces when cleaved from the LF-specific peptide substrate by LF activity. In certain aspects, the fluorescent dye moiety is a non-protein organic fluorophore. The molecular weight of the non-protein organic fluorophore may vary, ranging in some instances from 50 Da to 5 kDa, such as 75 Da to 1 kDa, including 80 Da to 800 Da.

In certain embodiments, a non-protein organic fluorophore may include a molecule belonging to any of the following chemical families: xanthene derivatives (such as fluorescein, rhodamine, Oregon green, eosin, Texas red, etc.); fluorescein derivatives (such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC(XRITC)); acridine derivatives (such as acridine orange, acridine yellow, acridine red, acridine isothiocyanate, proflavin, etc.); quinone-imine derivatives (such as azines, oxazines, and thiazines); cyanine derivatives (such as cyanine, indocarbocyanine, oxacarbocyanine, thiacarbocyanine, merocyanine, etc.); naphthalene derivatives (such as dansyl and prodan derivatives); coumarin and derivatives thereof (e.g., 7-amino-4-methylcoumarin (i.e., AMC, Coumarin 120), 7-amino-4-trifluoromethylcouluarin (i.e., coumaran 151)); azo derivatives; oxadiazole derivatives (such as pyridyloxazole, nitrobenzoxadiazole benzoxadiazole, etc.); anthracene derivatives; anthraquinones (such as DRAQ5, DRAQ7 CyTRAK Orange, etc.); pyrene derivatives (such as pyrene butyrate, succinimidyl 1-pyrene butyrate, cascade blue, etc.); oxazine derivatives (such as Nile red, Nile blue, cresyl violet, oxazine 170, etc.); arylmethane derivatives (such as auramine, crystal violet, malachite green, etc.); tetrapyrrole derivatives (such as porphin, phthalocyanine, bilirubin, etc.); squaraines (e.g., bis-squaring, mono-squaraine), squarylium, 2-[6-[4-(dimethylamino)phenyl]-1,3,5-hexatrienyl]-3-ethyl-benzothiazolium perchlorate (LDS 820), (2-(6-(p-dimethylaminophenyl)-2,4-neopentylene-1,3,5-hexatrienyl)-3-ethylbenzothiazolium perchlorate) (LDS 821), fluoranthene, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS; anthranilamide, 5',5''-dibromopyrogallol-sulfonephthalein (Bromopyrogallol Red); diethylenetriamine pentaacetate, 4,4'-diisothiocyanatodihydro-stilbene-2,2'-disulfonic acid, 4,4'-diisothiocyanatostilbene-2,2'-disulfonic acid, [4-dimethylamino]naphthalene-1-sulfonyl chloride (DNS, dansyl chloride), 4-(4'-dimethylaminophenylazo)benzoic acid (DABCYL); 4-dimethylaminophenylazophenyl-4'-isothiocyanate (DABITC), erythrosin and derivatives thereof (such as erythrosin B and erythrosin isothiocyanate), fluorescamine and derivatives thereof, Malachite Green isothiocyanate, 4-methylumbelliferone, ortho cresolphthalein, nitrotyrosine, pararosaniline, Phenol Red, B-phycoerythrin, o-phthaldialdehyde, Reactive Red 4 (Cibacron™ Brilliant Red 3B-A), rosolic acid and terbium chelate derivatives, and so forth. A number of dyes are described in "Fluorescent Dyes and Their Supramolecular Host/Guest Complexes with Macrocycles in Aqueous Solution" (Dsouza et al. Chem. Rev. 2011, 111, 7941-7980), where such dyes may be present in compositions described herein. In addition, the non-protein organic fluorophore may include one or more macrocyclic ligands.

In some cases, the detectable label is a chromophore that includes an aromatic dye, such as, but not limited to, aniline (e.g., p-nitroanilide), and p-nitrophenyl acetate.

In some cases, the detectable label is a coumarin, or derivative thereof, including, but not limited to, 7-amido-4-methylcoumarin, 7-amido-4-trifluoromethylcoumarin, and 7-amido-4-carbamoylmethylcoumarin.

In some cases, the detectable label is a rhodamine (e.g., rhodamine 110), or derivative thereof. Rhodamine can be mono-substituted or be bis-substituted. Thus, in some cases, the peptide substrate includes mono-substituted rhodamine that includes a peptide cleaved by lethal factor and containing an amino acid sequence of the present disclosure, covalently linked to rhodamine, wherein the rhodamine does not include any other peptide substituents. In some cases, the peptide substrate includes bis-substituted rhodamine, where a first and second peptides cleaved by lethal factor, each peptide containing the amino acid sequence of the present disclosure, are covalently linked to rhodamine at each of the primary amine groups of rhodamine, where the first and second peptide may or may not have the same sequence (and chirality) of amino acids. In some cases, the first and second peptides linked to a bis-substituted rhodamine contain the same sequence and/or chirality of amino acids.

Methods

Also provided herein is a method of making the present LF-specific peptide substrate, and a method of using the peptide substrate to detect *Bacillus anthracis* infection in a biological sample.

Method of Producing a Peptide Substrate

The peptide substrate of the present disclosure may be synthesized by any conventional method, including, but not limited to, those set forth in J. M. Stewart and J. D. Young, *Solid Phase Peptide Synthesis,* 2nd ed., Pierce Chemical Co., Rockford, Ill. (1984) and J. Meienhofer, *Hormonal Proteins and Peptides*, Vol. 2, Academic Press, New York, (1973) for solid phase synthesis and E. Schroder and K. Lubke, *The Peptides*, Vol. 1, Academic Press, New York. (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Either the amino or carboxyl group of the first amino acid, and any reactive side chain group may be protected. This protected amino acid is then either attached to an inert solid support, or utilized in solution, and the next amino acid in the sequence, also suitably protected, is added under conditions amenable to formation of the backbone linkage (e.g., amide linkage, ester linkage, etc.). The synthesis may occur from C-terminal to N-terminal sequence, from N-terminal to C-terminal sequence, or may occur in a mixed sequence. When used, the detectable label can be added during the solid-phase synthesis reaction, or as a later step in aqueous phase, as is known to those of skill in the art. After all the desired amino acids have been linked in the proper sequence, protecting groups and any solid support are removed to afford the crude polypeptide. The polypeptide is desalted and purified, such as chromatographically, to yield the final product.

In certain embodiments, the present peptide substrate is produced by synthesizing the an intermediate peptide that includes from the first to the penultimate amino acid of the peptide substrate (i.e., $X^1$-$X^2$-$X^3$-$X^4$-$X^5$-$X^6$ (SEQ ID NO:9)), releasing the intermediate from any solid support or blocking group at the C-terminus and reacting the free C-terminal amino acid with the last amino acid covalently linked to the detectable label (i.e., $X^{7*}$).

In certain embodiments, the present peptide substrate is produced by synthesizing the an intermediate peptide that includes the first to the last amino acid of the peptide substrate (i.e., $X^1$-$X^2$-$X^3$-$X^4$-$X^5$-$X^6$-$X^7$ (SEQ ID NO:10)), releasing the intermediate from any solid support or blocking group at the C-terminus and reacting the free C-terminal amino acid with the detectable label (i.e., Z).

In certain embodiments, the present peptide substrate is produced by synthesizing the entire peptide substrate, including the detectable label, on a solid support. In some cases, the detectable label is attached to the solid support, e.g., where the detectable label is 7-amido-4-carbamoylmethylcoumarin.

In some cases, peptides are synthesized according to standard solid-phase methodologies, such as may be performed on an Applied Biosystems™ Model 430A peptide synthesizer (Applied Biosystems™, Foster City, Calif.), according to manufacturer's instructions. Any other suitable methods of synthesizing peptides or peptidomimetics, either by solid phase methodologies or in liquid phase, may be used.

Alternatively, the peptide portion of the peptide substrate can be produced via standard recombinant DNA technology. A DNA sequence encoding the desired amino acid sequence may be cloned into an appropriate expression vector and used to transform a host cell so that the cell expresses the encoded peptide sequence. Any suitable methods of cloning, expression, and purification of recombinant peptides may be used. See, for example, Green and Sambrook, MOLECULAR CLONING: A LABORATORY MANUAL, 4$^{th}$ edition (2012), Methods in Enzymology, Vol. 152: Guide to Molecular Cloning Techniques (Berger and Kimmel (eds.), San Diego: Academic Press, Inc. (1987)), or Current Protocols in Molecular Biology, (Ausubel, et al. (eds.), Greene Publishing and Wiley-Interscience, New York (1987).

Method of Detecting

A further aspect of the present disclosure includes a method of detecting B. anthracis lethal factor in a biological sample using the LF-specific peptide substrate as described herein. The use of the present LF-specific peptide substrate allows rapid, specific, sensitive and accurate detection of LF in a sample of interest.

Anthrax LF may be a polypeptide having an amino acid sequence at least 75%, e.g., at least 80%, at least 85%, at least 90%, at least 95%, at least 98%, or 100% sequence identity to the amino acid sequence set forth in SEQ ID NO: 11 (FIG. 11A). In some cases, anthrax LF may be a polypeptide having an amino acid sequence at least 75%, e.g., at least 80%, at least 85%, at least 90%, at least 95%, at least 98%, or 100% sequence identity to positions 34-809 of the amino acid sequence set forth in SEQ ID NO: 11 (FIG. 11A). The anthrax LF may be synthetically produced using any convenient recombinant DNA technology. In some cases, anthrax LF is produced from a biological source of anthrax LF (e.g., a culture of B. anthracis, a biological sample known to contain B. anthracis) and may or may not be purified using an LF-specific binding partner (e.g., an LF-specific antibody).

An implementation of the present method includes contacting a test sample derived from a biological sample with an anthrax lethal factor-specific peptide substrate, as described herein, under conditions sufficient for anthrax lethal factor to cleave the substrate and generate a cleaved product. The level of the cleaved product in the test sample may then be measured using any suitable method, such as high-pressure liquid chromatography or fluorometry. The measured level of the cleaved product provides an indication of whether anthrax lethal factor is present in the biological sample or not, and/or of the concentration of lethal factor in the biological sample. The determination of the presence and/or concentration of lethal factor in the biological sample may be done by measuring at a single time point, or a plurality of time points (e.g., two or more time points) after addition of the substrate to the test sample.

The biological sample may be any suitable sample where the presence of anthrax lethal toxin is to be determined. The biological sample may be whole blood, plasma, serum, extracellular fluid, cytosolic fluid, or tissue and other fluids. Techniques known in the art may be suitably employed to homogenize, liquefy, or otherwise process the sample for analysis. In instances when tissue is sampled, the sample may be frozen and assayed remotely in time and place.

The biological sample may be obtained from an individual suspected of having been or known to be exposed to B. anthracis. The exposure may be any suitable exposure that can result in infection of the individual by B. anthracis. In some cases, the exposure is by respiratory (e.g., by inhalation of anthrax spores), cutaneous (e.g., skin contact with surfaces that contain anthrax spores), or gastrointestinal (e.g., ingesting food stuff that is tainted with anthrax). The biological sample may be obtained from the individual at any stage after the exposure or after infection. In some cases, the biological sample is obtained at an early stage of the infection or soon after exposure. Thus, in such cases, the biological sample is a sample obtained from the individual at or earlier than 7 days, e.g., at or earlier than 4 days, at or earlier than 3 days, at or earlier than 60 hours, at or earlier than 48 hours, including at or earlier than 36 hours after exposure to or infection with B. anthracis by the individual, and obtained at or after 12 hours, e.g., at or after 24 hours, at or after 36 hours, at or after 48 hours, including at or after 60 hours after exposure to or infection with B. anthracis by the individual. In some embodiments, the biological sample is a sample obtained from the individual between 12 hours and 7 days, e.g., between 24 hours and 4 days, between 24 hours and 3 days, including between 24 hours and 2 days after exposure to or infection with B. anthracis by the individual.

In certain embodiments, the biological sample is obtained from an individual before symptoms of B. anthracis infection are observed in the individual. The symptoms may include any suitable symptoms of B. anthracis infection. In some cases, symptoms of cutaneous anthrax infection include one or more bumps or blisters that may be itchy; a swelling around a sore; and/or a skin sore with a black center that may be painless, appearing after the blisters or bumps. In some cases, symptoms of gastrointestinal anthrax infection include fever; chills; diarrhea; bloody diarrhea; swelling of the neck or neck glands; headache; sore throat; flushing; red eyes; painful swallowing; stomach pain; hoarseness; fainting; nausea; vomiting; bloody vomiting; and/or swelling of the abdomen. In some cases, symptoms of inhalation anthrax infection include fever; chills; nausea; vomiting; stomach pain; chest discomfort; headache; shortness of breath; sweats; confusion; dizziness; extreme fatigue; cough; and/or body aches. In some cases, symptoms of injection anthrax infection include fever; chills; one or more bumps or blisters that may be itchy; a swelling around a sore; and/or a skin sore with a black center that may be painless, appearing after the blisters or bumps; and/or abscesses deep under the skin or muscle at the site of injection.

In some cases, the biological sample includes foodstuffs for human or non-human animal consumption. For example, the biological sample may be obtained from meat processing plants.

The biological sample may be processed to derive a test sample suitable for use in the present method. In some cases, the biological sample is in a suitable condition for use as the test sample. In some cases, at least a portion of the biological sample is diluted in an appropriate assay buffer. The extent of dilution of the biological sample in the test sample may vary, and may depend on various factors, such as the amount of LF in the sample, the amount of non-LF proteases in the sample, etc. In some cases, the test sample includes the biological sample at about 50% or less, e.g., about 40% or less, about 30% or less, about 25% or less, including about 20% or less, and includes the biological sample at about 1% or more, e.g., about 5% or more, about 7% or more, including about 10% or more, by volume. In some cases, the test sample includes the biological sample in a range of 1 to 50%, e.g., 1 to 40%, 5 to 30%, including 5 to 25%, by volume. In some cases, the biological sample that is diluted in assay buffer is plasma or serum, e.g., plasma or serum obtained from an individual suspected of having been or known to be exposed to B. anthracis.

The biological sample may be diluted in any suitable medium to prepare the test sample. In some cases, the biological sample is diluted in a buffer to prepare the test sample. Any suitable aqueous buffer may be used to dilute the biological sample, including, but not limited to, 4-(2-hydroxyethyl)-1-piperazineethanesulfonic acid (HEPES) buffered saline (HBS), phosphate buffered saline (PBS), 3-(N-morpholino)propanesulfonic acid (MOPS), etc.

In some cases, the test sample is enriched for lethal factor. The lethal factor may be enriched by any suitable method to produce the test sample. In some cases, the biological sample is processed to enrich for lethal factor. In some cases, lethal factor is enriched by contacting the biological sample with an anthrax LF-specific binding partner, separating LF bound to the binding partner from the rest of the biological sample, thereby enriching the lethal factor. In some cases, the lethal factor may be eluted from the binding partner to release LF into solution (e.g., the assay buffer).

The anthrax LF-specific binding partner may be any suitable binding partner that binds specifically to LF, where the binding partner does not substantially inhibit the catalytic activity of LF. In some cases, the binding partner is a LF-specific antibody (i.e., an antibody that specifically recognizes and binds LF). The LF-specific antibody may be any suitable antibody, including those provided by List Biological Laboratories; HyTest, Ltd; Santa Cruz Biotechnology; Abcam; and ThermoFisher Scientific. The antibody may be polyclonal or monoclonal. In some cases, the binding partner is a non-antibody polypeptide that specifically binds LF. In some cases, the binding partner is derived from *B. anthracis* protective antigen (PA), such as PA63. PA63 may include a polypeptide with an amino acid sequence at least 75%, e.g., at least 80%, at least 85%, at least 90%, at least 95%, at least 98%, or 100% sequence identity to positions 197-764 of the amino acid sequence set forth in SEQ ID NO:12 (FIG. 11B).

In certain embodiments, the anthrax LF-specific binding partner is bound to a solid support, e.g., an insoluble solid support. The solid support may be any suitable solid support for binding and purifying LF from a biological sample. In some cases, the solid support is a bead, a column or a multi-well plate. A solid support bead may be any suitable bead, including magnetic bead, agarose bead, sepharose bead, nickel bead, or beads of other materials known in the art. Numerous commercial sources are available for protein purification beads including New England Biolabs, Quiagen, EMD Millipore and ThermoFisher Scientific.

The anthrax LF-specific binding partner may be attached to the solid support using any suitable method. In certain embodiments, the solid support may be coated with an antibody-capturing reagent, e.g., protein G, protein A, or any other suitable antibody-capturing agent, and reacted with antibodies that recognize and bind LF, to capture and enrich the LF in the biological sample. In some cases, nonporous magnetic beads may be coated with an antibody-capturing reagent, e.g., protein G, protein A, etc., and reacted with antibodies that recognize and bind LF to capture the LF from the biological sample. In some cases, wells of a suitable multi-well plate (e.g., a 96-well plate coated with an antibody-capturing reagent) may be coated with a solution of LF-specific antibodies to attach the antibodies to the surface of the wells. The plates may then be washed with an elution buffer (e.g., 0.1 M glycine-HCl), followed by saline buffer.

In some embodiments, the LF-specific binding partner, e.g., LF-specific antibody, is covalently bound to a solid support. The LF-specific binding partner may be bound covalently to a solid support via any suitable covalent linkage. In some cases, the solid support is an activated support, e.g., activated bead, configured to react with the LF-specific binding partner such that the LF-specific binding partner is covalently bound to the solid support and retains binding activity for LF. The activated support may be an N-hydroxysuccinimide ester (NHS)-activated support, aldehyde-activated support, azlactone-activated support, carbonyl diimidazole (CDI)-activated support, or a hydrazide-activated support, etc.

The assay buffer may be any suitable assay buffer for carrying out the LF cleavage reaction and/or for measuring the level of the cleavage product. The assay buffer may include any suitable ingredients. In some cases, the assay buffer is a peptide-substrate specific assay buffer. A peptide substrate-specific assay buffer may include HEPES, TWEEN-20 (polysorbate 20), each at any suitable amount, and may or may not include $ZnCl_2$, at any suitable amount. In certain embodiments, the peptide substrate-specific assay buffer includes HEPES in a range of 5-50 mM, e.g., 10-30 mM. In certain embodiments, the peptide substrate-specific assay buffer includes TWEEN-20 (polysorbate 20) in a range of 0.01-1%, e.g., 0.05-0.5%. In certain embodiments, the peptide substrate-specific assay buffer includes $ZnCl_2$ in range of 5-50 μM, e.g., 10-30 μM. The peptide substrate-specific assay buffer may have any suitable pH. In certain embodiments, the peptide substrate-specific assay buffer has a pH in the range of 7.0 to 9.0, e.g., 7.5 to 8.5, including 7.8 to 8.3.

In certain embodiments, the peptide substrate-specific assay buffer for a peptide substrate having 7-amido-4 methylcoumarin as a detectable label includes HEPES in a range of 5-50 mM, e.g., 10-30 mM. In certain embodiments, the peptide substrate-specific assay buffer for a peptide substrate having 7-amido-4 methylcoumarin as a detectable label includes TWEEN-20 (polysorbate 20) in a range of 0.01-1%, e.g., 0.05-0.5%. In certain embodiments, the peptide substrate-specific assay buffer for a peptide substrate having 7-amido-4 methylcoumarin as a detectable label has a pH in the range of about 7.9 to about 8.1.

In certain embodiments, the peptide substrate-specific assay buffer for a peptide substrate having 7-amido-4-trifluoromethyl-coumarin as a detectable label includes HEPES in a range of 5-50 mM, e.g., 10-30 mM. In certain embodiments, the peptide substrate-specific assay buffer for a peptide substrate having 7-amido-4-trifluoromethyl-coumarin as a detectable label includes TWEEN-20 (polysorbate 20) in a range of 0.01-1%, e.g., 0.05-0.5%. In certain embodiments, the peptide substrate-specific assay buffer for a peptide substrate having 7-amido-4-trifluoromethyl-coumarin as a detectable label has a pH in the range of about 8.1 to about 8.2.

In certain embodiments, the peptide substrate-specific assay buffer for a peptide substrate having rhodamine as a detectable label includes HEPES in a range of 5-50 mM, e.g., 10-30 mM. In certain embodiments, the peptide substrate-specific assay buffer for a peptide substrate having rhodamine as a detectable label includes TWEEN-20 (polysorbate 20) in a range of 0.01-1%, e.g., 0.05-0.5%. In certain embodiments, the peptide substrate-specific assay buffer for a peptide substrate having rhodamine as a detectable label includes $ZnCl_2$ in range of 5-50 μM, e.g., 10-30 μM. In certain embodiments, the peptide substrate-specific assay buffer for a peptide substrate having rhodamine as a detectable label has a pH in the range of about 7.9 to about 8.1.

Measuring the level of cleavage product may be carried out using any suitable method, depending on the peptide substrate, and the nature of the detectable label, if any. In some cases, the measuring includes using fluorescence or colorimetric spectroscopy, high-pressure liquid chromatography (HPLC) and/or mass spectrometry. Fluorescence spectroscopy may include any suitable spectroscopic methods, such as fluorometry using, e.g., a plate reader, or fluorescence microscopy, etc. Colorimetric assays may be performed in similar ways to fluorescence spectroscopy. HPLC may be performed using any suitable method. In some cases, where the peptide substrate includes a fluorogenic or chromogenic detectable label, the elution coming off of the HPLC column is assayed using a detector, e.g., a fluorescence detector or a colorimetric detector, tuned to the appropriate wavelength to detect the detectable label. In some cases, where the cleavage product is identified by mass, mass spectrometry may be used to measure the level of the cleavage product in the test sample. The mass spectrometry may be any suitable mass spectrometry method, including, but not limited to, sector field mass spectrometry, quadrupole mass spectrometry, ion trap mass spectrometry, electro-spray ionization liquid chromatography tandem mass spectrometry (LC-MS/MS), time-of-flight (TOF) mass spectrometry, matrix-assisted laser desorption ionization (MALDI)-TOF, etc.

The level of cleavage product measured in the sample may be represented by any suitable value that can be obtained by the method of measurement used. The level may be represented as an arbitrary intensity unit (e.g., an arbitrary fluorescence intensity unit), a normalized or relative intensity unity (e.g., a normalized or relative fluorescence intensity unit), an absolute concentration, an area under a curve (e.g., area under a peak curve), or any other suitable value. In some cases, where the level of cleavage product is measured using a fluorimeter, the level is represented by a normalized or relative fluorescence intensity unit. In certain embodiments, where the level of cleavage product is measured using HPLC and a fluorescence detector, the level is represented by area under the peak curve.

The present method may in some cases include comparing the measured level of the cleavage product with a reference level, where LF is determined to be present in the sample if the measured level is equal to or above the reference level, and determined not to be present if the measured level is not above the reference level. The reference level may be a predetermined reference level, or may be obtained by performing the assay on a reference sample that contains a known amount of LF. In some cases, the reference sample contains no LF.

In some cases, the method includes measuring a concentration of the lethal factor in the test sample. In some embodiments, the level of lethal factor may be determined by comparing the measured level with a reference level, as described above. In some cases, the level of lethal factor in the sample is determined using multiple measurements of the level of cleavage product carried out over multiple time points after adding the substrate to the test sample, and analyzing the measurements. In such cases, the rate of change in the level of cleavage product provides a measure of the concentration of lethal factor in the test sample. In some cases, the conversion factor between the rate of change in the level of cleavage product and the concentration of lethal factor in the test sample is a predetermined conversion factor. In some cases, the conversion factor between the rate of change in the level of cleavage product and the concentration of lethal factor in the test sample is obtained by performing the assay on one or more reference samples that contain known amounts of LF and measuring the rate of change in the level of cleavage product in the reference samples.

The multiple time points may be taken over the course of 48 hours or less, e.g., 36 hours of less, 24 hours or less, including 12 hours or less, and may be taken immediately after, 30 minutes or more, e.g., 45 minutes or more, 1 hour or more, including 1.5 hours or more after mixing the peptide substrate with the test sample. In some embodiments, the multiple time points are taken at times points immediately after mixing the peptide substrate with the test sample to 48 hours, e.g., 30 minutes to 36 hours, 1 hour to 24 hours, including 1 hour to 12 hours after mixing the peptide substrate with the test sample.

The method of the present disclosure can be a sensitive method of detecting the presence of anthrax LF in a biological sample. In some cases, the present method can detect LF present in a biological sample at 50 ng/ml or less, e.g., 20 ng/ml or less, 10 ng/ml or less, 5 ng/ml or less, 1 ng/ml or less, 500 pg/ml or less, 100 pg/ml or less, 50 pg/ml or less, 20 pg/ml or less, 10 pg/ml or less, down to about 5 pg/ml, and can detect LF present in a biological sample at about 5 pg/ml or more, 10 pg/ml or more, 20 pg/ml or more, 40 pg/ml or more, 60 pg/ml or more, 80 pg/ml or more, 150 pg/ml or more, 300 pg/ml or more, 600 pg/ml or more, including 1000 pg/ml or more. In some cases, the method can detect LF present in a biological sample in the range of about 5 pg/ml to 50 ng/ml, e.g., about 5 pg/ml to 1 ng/ml, about 5 pg/ml to 100 pg/ml, about 5 pg/ml to 50 pg/ml, about 5 pg/ml to 20 pg/ml.

The present method can be a sensitive method to detect LF in a biological sample without enriching the sample for LF to derive the test sample. In such cases, the method may include using fluorimetry (e.g., using a microplate reader) to measure the level of cleavage product in the test sample. In some cases, the present method can detect the presence of LF in a biological sample, without enriching for LF, at 50 ng/ml or less, e.g., 20 ng/ml or less, 10 ng/ml or less, 5 ng/ml or less, down to about 1 ng/ml, and can detect the presence of LF in a biological sample, without enriching for LF, at about 1 ng/ml or more, e.g., 2 ng/ml or more, 5 ng/ml or more, including 10 ng/ml or more. In some cases, the present method can detect the presence of LF in a biological sample, without enriching for LF, in a range of about 1 ng/ml to 50 ng/ml, e.g., about 1 ng/ml to 20 ng/ml, about 1 ng/ml to 10 ng/ml, including about 1 ng/ml to 5 ng/ml.

The sensitivity of the method may be expressed as the limit of detection, which can be defined as the concentration of LF that can be detected with 99% confidence to be greater than zero, as defined by background measurements. The average background value is obtained by measuring a sample that does not contain any LF and to which the peptide substrate was added.

Utility

The present peptide substrates and methods of use thereof find use in a variety of situations where it is desirable to detect the presence of *B. anthracis* in a sample. Thus in some cases, the present peptide substrates and methods of use thereof may be used to diagnose a *B. anthracis* infection in an individual (e.g., a patient) who may have been exposed to *B. anthracis* by inhalation, cutaneous contact and/or ingestion. In such cases, a method of detecting anthrax lethal factor in a biological sample, as described above, may include obtaining a biological sample, e.g., blood, serum, plasma, etc., from an individual who is suspected of having been exposed to *B. anthracis*. In certain embodiments, the present method may be used to detect lethal factor in a biological sample obtained from an individual who is suspected of having been exposed to *B. anthracis* but who does not exhibit symptoms of an anthrax infection.

In some embodiments, a method of diagnosing a *B. anthracis* infection in an individual may include performing a method of detecting anthrax lethal factor in a first biological sample obtained from the individual, as described above, in conjunction with a method for diagnosing the individual for anthrax infection. In some embodiments, a method of diagnosing a *B. anthracis* infection in an individual may include performing a method of detecting anthrax lethal factor in a first biological sample obtained from the individual, as described above, and when the biological sample is determined to contain anthrax lethal factor, diagnosing the individual for *B. anthracis* infection. The diagnosing may include any suitable method of diagnosing an individual for anthrax infection. In some cases, the diagnosing may include performing clinical observations for symptoms of anthrax infection. In some cases, the diagnosing may include performing an assay to detect the presence *B. anthracis*, as is known in the art, in a second biological sample obtained from the individual. The first and second biological samples may be the same or different biological samples. Examples of methods for diagnosing anthrax infection include, e.g., examining the individual's history of exposure (e.g., contact with a white powder or contact with infected animals or humans), evidence of systemic inflammation (e.g., the presence of fever, tachypnea, or tachycardia), detection of the anthrax protective antigen (PA) using anti-PA IgG detection by ELISA, PCR analyses, immunohistochemical staining of tissues, MacFaydean polychrome methylene blue staining of serum (e.g., blood) for the detection of anthrax bacilli, chest x-rays (e.g., to detect mediastinal widening, pleural effusion, or infiltrates), computed tomography (CT) scans (e.g., to detect mesenteric adenopathy), or culture growths.

In some cases, the present peptide substrates and methods of use thereof may be used to provide a prognosis of a known *B. anthracis* infection in an individual. In such cases, a method of detecting anthrax lethal factor in a biological sample, as described above, may include obtaining a biological sample, e.g., blood, serum, plasma, etc., from an individual who is diagnosed with a *B. anthracis* infection. In some cases, the present peptide substrates and methods of use thereof may be used to monitor the progress of a treatment regimen for a *B. anthracis* infection in an individual. In such cases, a method of detecting anthrax lethal factor in a biological sample, as described above, may include obtaining a biological sample, e.g., blood, serum, plasma, etc., from an individual who is diagnosed with a *B. anthracis* infection and has received a treatment for the infection. In some cases, the biological sample may be a sample obtained from the individual before and after receiving the treatment for the *B. anthracis* infection.

The present peptide substrates and methods of use thereof may also find use in screening samples for *B. anthracis* anthrax infection in foodstuffs by detection of LF. Thus in some cases, the present peptide substrates and methods of use thereof may be used to screen samples from meat processing plants, raw food material, processed food, drinking water, etc. In such cases, a method of detecting anthrax lethal factor in a biological sample, as described above, may include obtaining a biological sample from a meat processing plant, raw food material, processed food, drinking water, etc.

Kits

Also provided herein is a kit that includes the present anthrax lethal factor-specific peptide substrate and that find use in performing methods such as those described herein. The kit may contain the present anthrax lethal factor-specific peptide substrate, as described above, and a standardization element. The standardization element may be any suitable element that can provide a guide to interpret the levels of cleavage product measured using the methods of the present disclosure, and to determine whether and/or how much lethal factor is present in a biological sample.

In some cases, the standardization element is one or more positive reference samples containing a known amount of lethal factor. The positive reference samples may be used to derive a conversion chart that shows the relationship between the measured level of cleavage product and/or the rate of change in the level of cleavage product, and the concentration of lethal factor in a biological sample.

In some cases, the standardization element is a negative reference sample, e.g. plasma, that does not contain lethal factor. The negative reference sample may be used to derive the background level of measurement. The background level can serve as a reference value above which a measured level of cleavage product in a test sample indicates presence of lethal factor in the biological sample.

In some cases, the standardization element is a standardization chart or table showing the relationship between the measured level of cleavage product and/or the rate of change in the level of cleavage product, and the concentration of lethal factor in a biological sample. The standardization chart or table may also indicate a background level of measurement, in the absence of lethal factor in a sample.

The standardization chart or table may be provided in any convenient medium, e.g., on paper, compact disc (CD), digital versatile disc (DVD), flash drive, Blue-ray Disc™, etc., or may be provided as an internet web address, e.g., a Uniform Resource Identifier (URL) on the medium that the user can type in a web browser to access a standardization chart or table stored at a remote location, e.g., a remote server.

In some cases, the kit includes an assay buffer that is specific for the peptide substrate, as described above. In some cases, the kit includes an enrichment element containing lethal factor-specific binding partners (e.g., LF-specific antibodies, PA63). The enrichment element may include a solid support to which the lethal factor-specific binding partners are bound. The solid support may be a bead, column or a multi-well plate, as described above.

In some cases, the present kit includes instructions for how to use the present peptide substrate. The instructions for practicing the subject methods are generally recorded on a suitable recording medium. For example, the instructions may be printed on a medium, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable medium.

The components of the present kit may be provided in separate containers, or two or more components of the kit may be provided in the same container, where appropriate.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., nl, nanoliter(s); ng, nanogram(s); pg, pictogram(s); ml, milliliter(s); mM, millimolar; μM, micromolar; s or sec, second(s); min, minute(s); h or hr, hour(s); aa, amino acid(s); T, temperature; RFU, relative fluorescent unit(s) and the like.

Example 1: Materials and Methods

Anthrax lethal factor (Product #169), and the chicken IgY polyclonal anti-lethal factor (LF) antibody (Product #769A) are products of List Biological Laboratories, Inc ("LBL"). The C8 Starwell™ Maxi Nunc-Immuno™ Module Plates (cat#441653) used for LF antibody coating and the dimethyl sulfoxide (DMSO) (cat #TS-20684) were purchased from ThermoScientific. The 96-well, black, flat bottom, non binding plates used for the fluorescent plate assay were from Corning (cat #3991). Bovine plasma (cat #7310806) was purchased from Lampire Biological Laboratories.

Lethal Factor Substrate Design:

The substrate sequences were designed based on a 15-amino acid FRET peptide. The sequence of the FRET peptide, 7-methoxycoumarin-4-acetyl (Mca)-Arg-Arg-Lys-Lys-Val-Tyr-Pro-Tyr-Pro-Met-Glu-2,4-dinitrophenol (DNP)-Thr-Ile-Ala (SEQ ID NO: 1), is cleaved between the proline and tyrosine.

Six peptides with 5-7 amino acids were designed as potential substrates for LF (Table 1). All of the peptides were designed so that cleavage releases a fluorophore, either 7-amido-4-methylcoumarin, 7-amido-4-trifluoromethylcoumarin or rhodamine, resulting in a measurable increase in fluorescence which should be directly proportional to the amount of cleavage that has occurred. D-amino acids were substituted in some or all of the positions P7-P4 (Table 1).

LBL 10095, was synthesized containing a rhodamine fluorophore. Rhodamine can be substituted with two peptides per fluorophore. The peptide LBL 10108 containing the fluorophore 7-amido-4-trifluoromethylcoumarin was also evaluated in order to compare fluorophores.

TABLE 1

Fluorogenic substrates evaluated as potential LF substrates

| Substrate LBL# | P7 | P6 | P5 | P4 | P3 | P2 | P1 | Fluorophore | SEQ ID NO: |
|---|---|---|---|---|---|---|---|---|---|
| 10079 | Arg | Arg | Lys | Lys | Val | Tyr | Pro | 7-amido-4-methylcoumarin | 2 |
| 10081 | Arg | D-Arg | D-Lys | D-Lys | Val | Tyr | Pro | 7-amido-4-methylcoumarin | 3 |
| 10097 | D-Arg | D-Arg | D-Lys | D-Lys | Val | Tyr | Pro | 7-amido-4-methylcoumarin | 4 |
| 10100 | — | — | D-Lys | D-Lys | Val | Tyr | Pro | 7-amido-4-methylcoumarin | 5 |
| 10108 | Arg | D-Arg | D-Lys | D-Lys | Val | Tyr | Pro | 7-amido-4-trifluoromethylcoumarin | 6 |
| 10095 | (Arg | D-Arg | D-Lys | D-Lys | Val | Tyr | $Pro)_2$ | rhodamine | 7 |

All peptides shown in Table 1 were synthesized using standard solid phase techniques. The peptides were shown to be >95% pure by reverse phase HPLC/UV. The expected molecular weights were confirmed by mass spectrometry. The peptide content was determined by nitrogen analysis. The N-terminals of each peptide substrate were acetylated.

Sample Preparation:

Fluorogenic Substrates:

Stock solutions of the fluorogenic substrates shown in Table 1 were made based on the peptide content. All stock solutions were 5 mM in DMSO except for LBL 10095 which was made 1.6 mM in 70% DMSO. The substrates were subsequently diluted in appropriate optimized assay buffers: LBL 10079, 10081, 10097 and 10100 were diluted in 20 mM 4-(2-hydroxyethyl)-1-piperazineethanesulfonic acid (HEPES), pH 8.0 containing 0.1% TWEEN-20 (polysorbate-20); substrate LBL 10095 was diluted in 20 mM HEPES, pH 8.0 containing 0.1% TWEEN-20 (polysorbate-20) and 20 μM $ZnCl_2$; substrate LBL 10108 was diluted in 20 mM HEPES, pH 8.2 containing 0.1% TWEEN-20 (polysorbate-20).

Anthrax Lethal Factor in Plasma:

For the plate assays, the LF was dissolved in neat bovine plasma and diluted 1:10 in the appropriate assay buffers (see above). For the high-pressure liquid chromatography (HPLC) assays, the LF was added to neat bovine plasma and not diluted.

LF Activity Assays:

Microplate Reader:

For the initial screen of the six substrates shown in Table 1, assays were performed on a SPECTRAmax® GEMINI XS fluorescence microplate reader (Molecular Devices). The cleavage reaction was initiated by addition of the substrate. For each substrate the concentration was optimized to minimize background while maintaining measurable cleavage. For all experiments the time-dependent increase in fluorescence was monitored at 37° C. hourly for 5 or 6 hours followed by an additional 18 to 18.5 hr overnight incubation at ambient temperature. The excitation wavelength was set to 368 nm and emission to 452 nm with a cutoff filter at 435 nm for the 7-amido-4-methylcoumarin containing substrates. For the substrate containing 7-amido-4-trifluoromethylcoumarin (LBL 10108) the excitation wavelength was set to 372 nm and the emission to 489 nm with a cutoff filter at 420 nm. For the rhodamine-containing substrate, the excitation wavelength was set to 494 nm, the emission wavelength to 531 nm and a cutoff filter set to 515 nm was used.

HPLC:

The C8 Starwell™ Maxi Nunc-Immuno™ Module Plates were coated with 150 µl of a 10 µg/ml solution of a chicken affinity purified polyclonal IgY antibody to anthrax lethal factor (List Prod #769A). Plates were incubated with the IgY overnight at 2-8° C. and washed three times with 0.1M Glycine-HCl, pH 2.5. This wash was included to liberate residual LF retained after the affinity purification of the antibody and minimized the background observed in plasma samples that did not contain LF. After 6 washes with phosphate buffer saline (PBS) containing 0.05% TWEEN-20 (polysorbate-20) (PBST), the anti-LF coated wells were exposed to 300 µl of a series of LF concentrations in neat plasma. The plates were incubated at 22° C. for 2 hours. Plates were then washed 6 times with PBST and 250 µl of 1.25 µM LBL 10081 was added. The substrate LBL 10081 was determined to be the preferred substrate for detection in this assay. The reaction was allowed to proceed for 2, 3.5, and 5 hours at 37° C. and overnight at ambient temperature. At each time point 200 µl of the reaction mixture was removed from replicate wells and placed in HPLC sample vials.

HPLC was performed using a Zorbax Eclipse Plus C18 reverse phase column, 4.6×150 mm (Agilent) and a guard column containing the same resin in a Varian ProStar HPLC system (Agilent). Solvent A was 0.1% TFA in water and solvent B was 0.1% trifluoroacetic acid (TFA) in acetonitrile. The 16 minute HPLC method was as follows: 25% B for 0.75 minutes; 25 to 45% B in 4.75 minutes; 45 to 100% B in 0.75 minutes; 100% B for 3.75 minutes; 100 to 25% B in 0.67 minutes and 5.34 minute equilibration with 25% B. The column effluent was monitored using a Hitachi fluorescence detector with excitation set to 350 nm and emission at 450 nm to detect the free coumarin fluorophore cleaved from LBL 10081. The injection volume was 20 µl. The 7-amido-4-methylcoumarin peak retention time was 4.78 minutes.

Example 2: Evaluation of Six Potential Lethal Factor Substrates Using a Microplate Assay Evaluation of Six Potential Lethal Factor Substrates Using a Microplate Assay Cleavage of the four 7-amido-4-methylcoumarin-labeled substrates (2.5 µM) by 0.0, 0.5, 1, and 2 ng LF/ml assay buffer is shown in the bar graph of FIG. 1. In assay buffer all the substrates, except LBL 10100, showed an increase in fluorescence as the amount of LF was increased.

FIG. 1: Cleavage of Substrates in Assay Buffer.

Plot of the increase in fluorescence (relative fluorescence unit—RFU) after 5 hours at 37° C. as a function of LF concentration (ng/ml) for LBL 10100, LBL10081, LBL 10079 and LBL 10097. The microplate assay was used to obtain the results.

The minimum length for these peptides to serve as substrates for LF was 6 or 7 amino acids. Removal of 2 amino acids from the N-terminal, as was the case for LBL 10100, reduced hydrolysis by LF.

The chirality of the N-terminal Arg did not significantly affect the cleavage by LF. Aside from the high background, the cleavage of LBL 10097 with D-Arg at the N-terminal and LBL 10081 with L-Arg, are similar.

Cleavage of these substrates by LF was not impaired by the substitution of D-amino acids. For example, the amount of hydrolysis observed for LBL 10079, which does not contain any D-amino acids, and LBL 10081, which contains three D-amino acids, is similar. The significance of this will be apparent in the discussion of peptide cleavage in plasma. It was hypothesized that the substitution of D-amino acids may improve the stability of LBL 10081 in plasma by inhibiting its cleavage by non-specific plasma proteins.

Cleavage of Fluorescent Peptides by Lethal Factor in 1:10 Diluted Bovine Plasma

Figure 2:
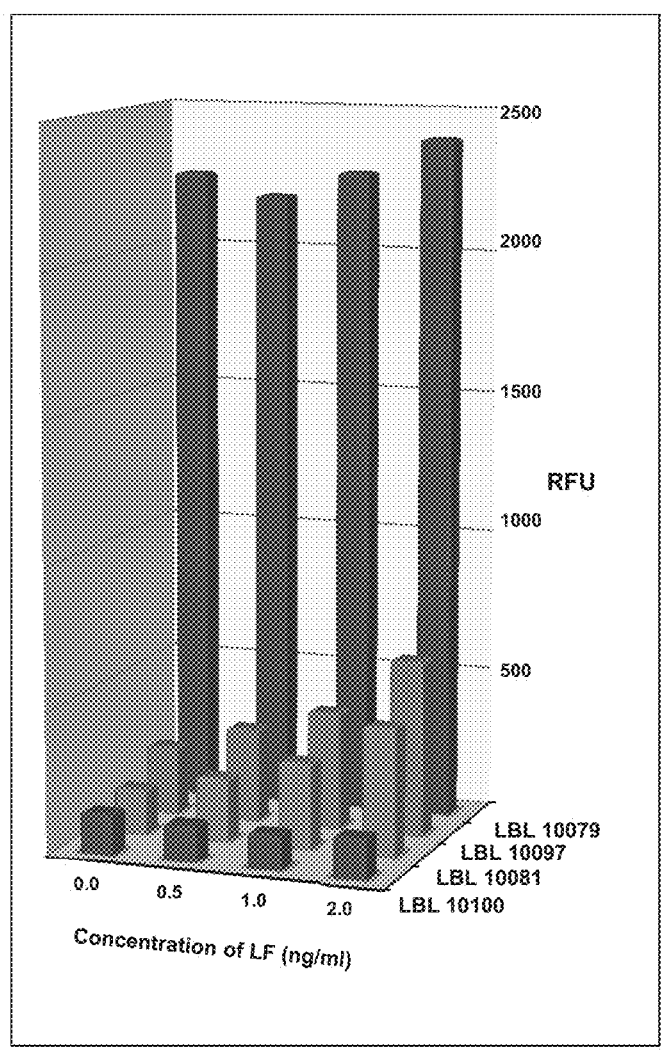
FIG. 2 is a graph showing measured fluorescence from LF-specific peptide substrates cleaved by LF in diluted plasma, according to embodiments of the present disclosure.

The bar graph in FIG. 2 shows data for cleavage of the four LF substrates containing the 7-amido-4-methylcoumarin fluorophore (2.5 µM) by LF in 1:10 diluted plasma.

FIG. 2: Cleavage of Substrates in 1:10 Diluted Bovine Plasma.

Plot of the increase in fluorescence (RFU) after 5 hours at 37° C. as a function of LF concentration (ng/ml) for LBL 10100, LBL10081, LBL 10097 and LBL 10079. The microplate assay was used to obtain these results.

There was a dramatic increase in fluorescence for LBL 10079 in plasma even in the absence of LF. This indicated that some plasma protease(s) is cleaving after the proline, releasing the fluorophore and giving rise to significant fluorescence. The cleavage did not correlate with the amount of LF in the sample.

The substitution of three or four of the amino acids with D-amino acids inhibited non-specific cleavage of LBL10081 and LBL 10097 by plasma proline proteases. LBL 10081 and LBL 10097 are hydrolyzed similarly. In addition, there was minimal increase in hydrolysis of these substrates in plasma without LF even after 5 hours incubation at 37° C. and after an additional 18 hours at ambient temperature (see FIG. 3). This was also true for samples containing ten times the amount of substrate in less diluted plasma, for example, 25 µM substrate in 1:5 diluted plasma.

Based on the data above, two additional substrates with different fluorophores were synthesized to determine whether changing the fluorophore was advantageous. Both peptides contain the same amino acid sequence as LBL 10081. LBL 10108 contained a 7-amido-4-trifluoromethyl-coumarin group at the C-terminal. LBL 10095 consisted of 2 peptides identical with LBL 10081 bound to a rhodamine at their C-terminals. The fluorescence increased as a function of LF concentration in 1:10 diluted plasma and neither peptide was cleaved in plasma in the absence of LF; however, there was no significant improvement in the sensitivity for either substrate when compared to LBL 10081 or LBL 10097.

Figure 3:
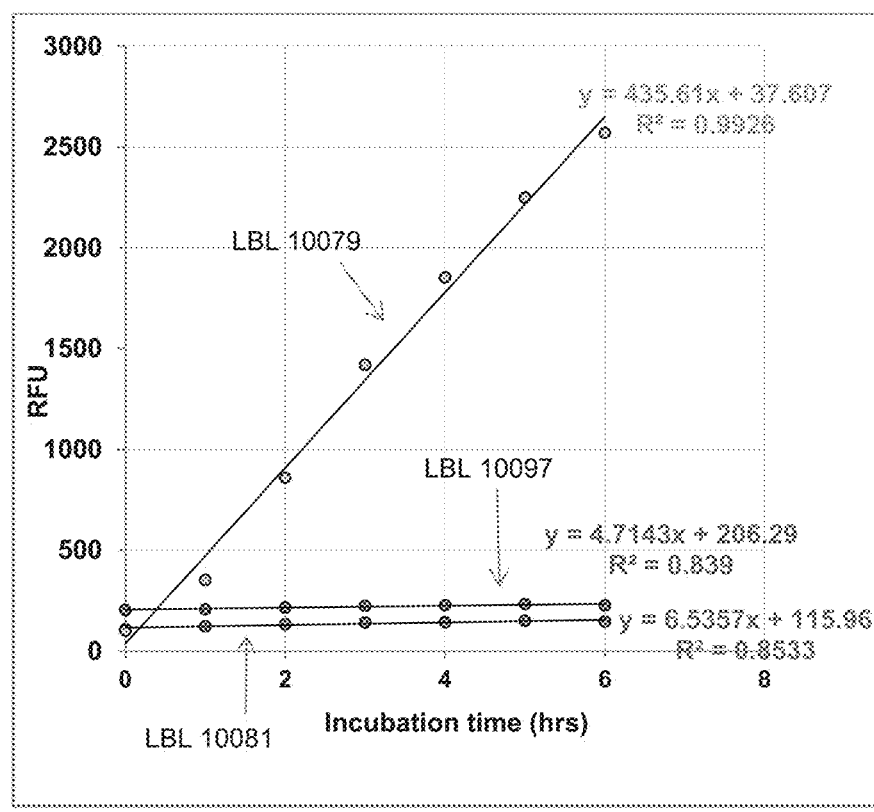
FIG. 3 is a graph showing measured fluorescence from LF-specific peptide substrates in diluted plasma, according to embodiments of the present disclosure.

The change in fluorescence for 2.5 µM LBL 10081 and 10097 in the presence of 1:10 diluted plasma without LF is compared to LBL 10079 in Table 1 and FIG. 3. The results of this microplate assay confirmed that LBL 10081 and LBL 10097 were specific for LF and that LBL 10079 was non-specifically cleaved by plasma proteases.

FIG. 3: Fluorescence (RFU) as a function of time for LBL 10081, LBL 10097 and LBL 10079 in 1:10 plasma at 37° C. in the absence of LF.

TABLE 1

Fluorescence observed for substrates
in 1:10 diluted plasma without LF.

| Time (hrs) | Temperature (° C.) | Substrate RFU | | |
|---|---|---|---|---|
| | | LBL 10081 | LBL 10097 | LBL 10079 |
| 0 | 37 | 108 | 204 | 102 |
| 1 | 37 | 123 | 208 | 353 |
| 2 | 37 | 134 | 217 | 860 |
| 3 | 37 | 142 | 225 | 1420 |
| 4 | 37 | 144 | 228 | 1854 |
| 5 | 37 | 151 | 234 | 2251 |
| 6 | 37 | 147 | 227 | 2571 |
| +15 | ambient | 163 | 243 | 4074 |
| +33 | ambient | 169 | 236 | 3920 |

Example 3: HPLC Method Using Antibody Capture to Concentrate the LF

Figure 4:
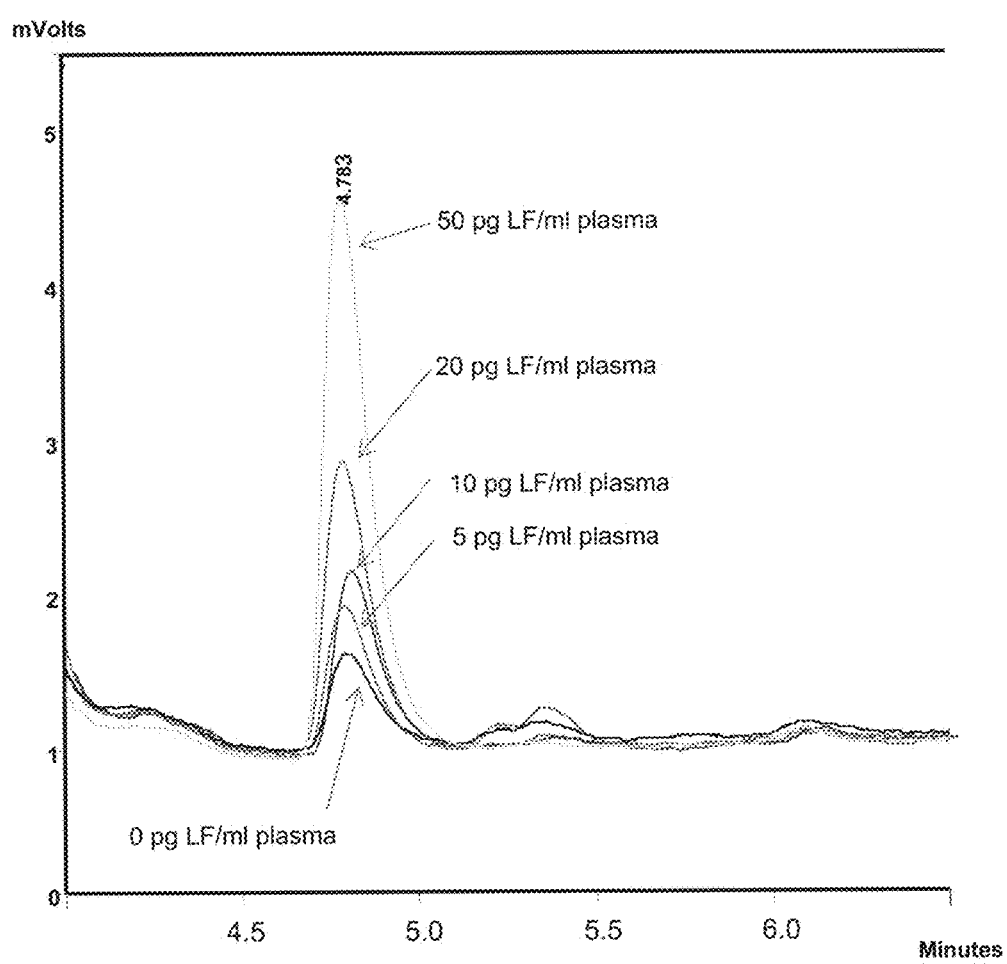
FIG. 4 is a graph showing high-pressure liquid chromatography (HPLC) traces of fluorescent cleavage products of LF-specific peptide substrates cleaved by LF enriched from neat plasma, according to embodiments of the present disclosure.

In order to optimize the detection of low levels of LF in plasma, the LF was enriched by using an affinity purified polyclonal antibody coated on a 96-well microtiter plate. In addition to enrichment of the LF, the method allowed capture of small amounts of LF from plasma without dilution. It was found that since the antibody had been affinity purified using LF there were low levels of residual LF remaining with the antibody. Several washes with 0.1M Glycine-HCl, pH 2.5 were included to liberate residual LF retained on the antibody coated plate. This wash minimized, but did not totally eliminate the background observed in plasma samples without LF. After addition of the substrate, LBL 10081, samples were monitored using HPLC with fluorescence detection after 2, 3.5 and 5 hrs of incubation at 37° C. Representative chromatograms are shown in FIG. 4. The HPLC data is summarized in Table 2.

FIG. 4: Chromatograms from the digestion of LBL 10081 by 0, 5, 10, 20, and 50 pg of LF/ml of neat plasma after 2 hours at 37° C.

TABLE 2

Detection of LF in neat plasma

| LF (pg/ml plasma) | rep | 2 hour digest | | 3.5 hour digest | | 5 hour digest | | Overnight digest (RT) | |
|---|---|---|---|---|---|---|---|---|---|
| | | Peak area | Average | Peak area | Average | Peak Area | Average | Peak area | Average |
| 0 | 1 | 5953 | 6006 | 8561 | 8815 | 9762 | 10645 | 18988 | 17136 |
| | 2 | 5935 | | 9425 | | 11276 | | 18212 | |
| | 3 | 5358 | | 8473 | | 9934 | | 15601 | |
| | 4 | 6567 | | 7481 | | 11062 | | 16934 | |
| | 5 | 6192 | | 8600 | | 11417 | | 17630 | |
| | 6 | 6031 | | 10350 | | 10421 | | 15451 | |
| 5 | 1 | 9414 | 9153 | 11466 | 12322 | 14786 | 14953 | 28485 | 26909 |
| | 2 | 8891 | | 13177 | | 15119 | | 25333 | |
| 10 | 1 | 10657 | 10315 | 16464 | 15906 | 22235 | 22309 | 36468 | 36248 |
| | 2 | 9972 | | 15348 | | 22382 | | 36027 | |
| 20 | 1 | 16883 | 15880 | 24042 | 24162 | 31594 | 32916 | 58250 | 57900 |
| | 2 | 14926 | | 24282 | | 34237 | | 57550 | |
| 50 | 1 | 33668 | 33662 | 49662 | 49053 | 67245 | 66657 | 136035 | 130221 |
| | 2 | 33656 | | 48443 | | 66068 | | 124407 | |

Figure 5:
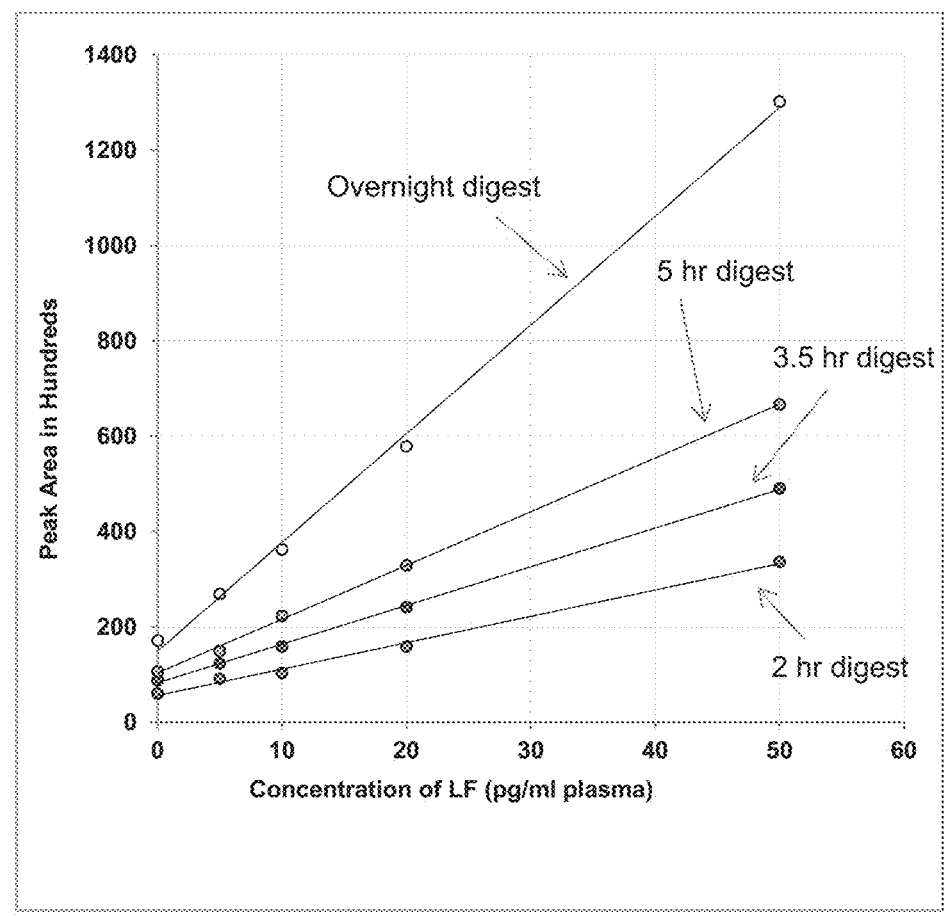
FIG. 5 is a graph showing HPLC peak areas of fluorescent cleavage products of LF-specific peptide substrates cleaved by LF enriched from neat plasma, according to embodiments of the present disclosure.

A plot of the peak areas as a function of LF concentration in the plasma is shown in FIG. 5. Analysis for each response curve is given in Table 3. The response at each time point was linear.

FIG. 5: Plot of peak areas versus concentration of LF (pg/ml plasma) for 2 hour, 3.5 hour, 5 hour and overnight digestion of LBL 10081.

TABLE 3

Slope, intercept, and correlation coefficients for each incubation time.

| | 2 hr digest | 3.5 hr digest | 5 hr digest | Overnight digest (RT) |
|---|---|---|---|---|
| Slope (Peak Area/pg LF) | 553 | 811 | 1127 | 2280 |
| Intercept (Peak area) | 5595 | 8256 | 10324 | 14916 |
| $R^2$ | 0.9954 | 0.9993 | 0.9992 | 0.9981 |
| Std deviation of the blanks | 394 | 973 | 708 | 1419 |
| 3x standard deviation + the average | 7189 | 11735 | 12768 | 21393 |
| LOD (pg/ml plasma) | 2.9 | 4.3 | 2.2 | 2.8 |

The limit of detection for each incubation time was estimated from the normal distribution (3 standard deviations) of blank plasma samples (0 pg LF; n=6), calculated as pg LF/ml plasma from the standard curve generated at each incubation time. This data is shown in Table 3. The results indicated that the limit of detection at all time points was less than 5 pg LF/ml of neat plasma.

Kinetic Analysis of the LF Activity by HPLC.

Figure 6:
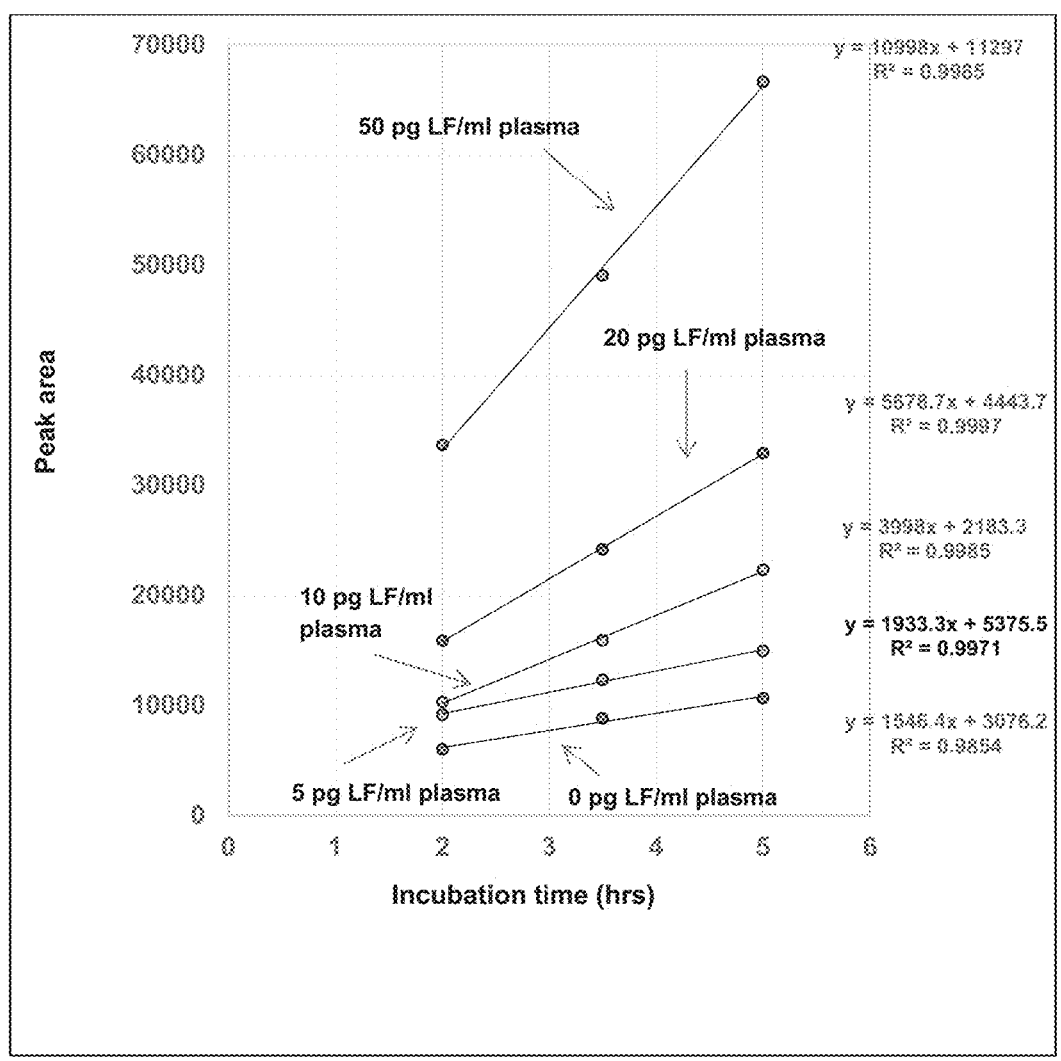
FIG. 6 is a graph showing HPLC peak areas, as a function of time, of fluorescent cleavage products of LF-specific peptide substrates cleaved by LF enriched from neat plasma, according to embodiments of the present disclosure.
Figure 7:
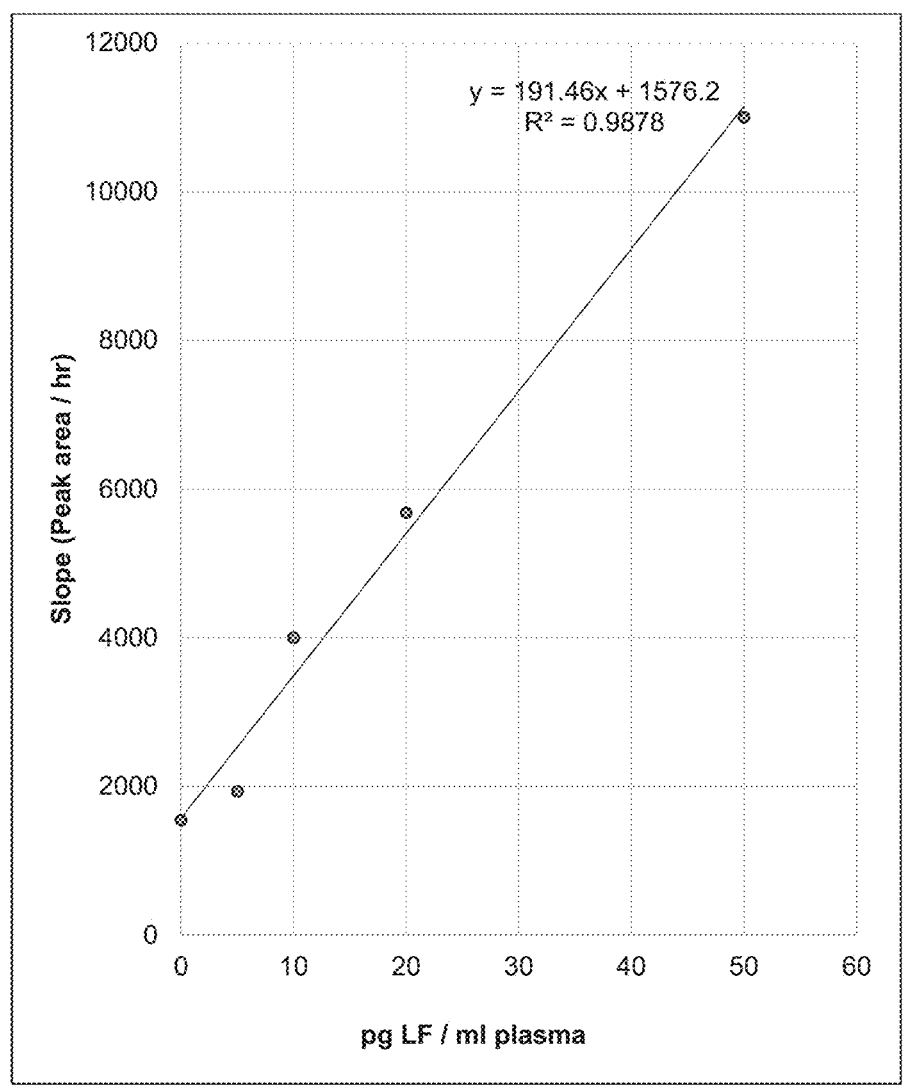
FIG. 7 is a graph showing the relationship between the slope of HPLC peak area change over time and LF concentration, according to embodiments of the present disclosure.

The amount of LF in an unknown sample could be determined from any single time point as shown above. However, such results might be subject to false positives due to uncertain background fluorescence. Alternately, the results could be obtained by monitoring the reaction rate, i.e. the increase in peak area as a function of time (FIG. 6). Each concentration of LF yielded a unique slope (rate) which was proportional to the concentration (FIG. 7). The limit of detection by this method was also around 5 pg LF/ml neat plasma.

FIG. 6: Plot of peak area versus incubation time for 0, 5, 10, 20, and 50 pg/ml plasma.

FIG. 7: Plot of the slopes as a function of the concentration of LF (pg/ml plasma).

Example 4: Rapid Microplate Assay Method

Figure 8:
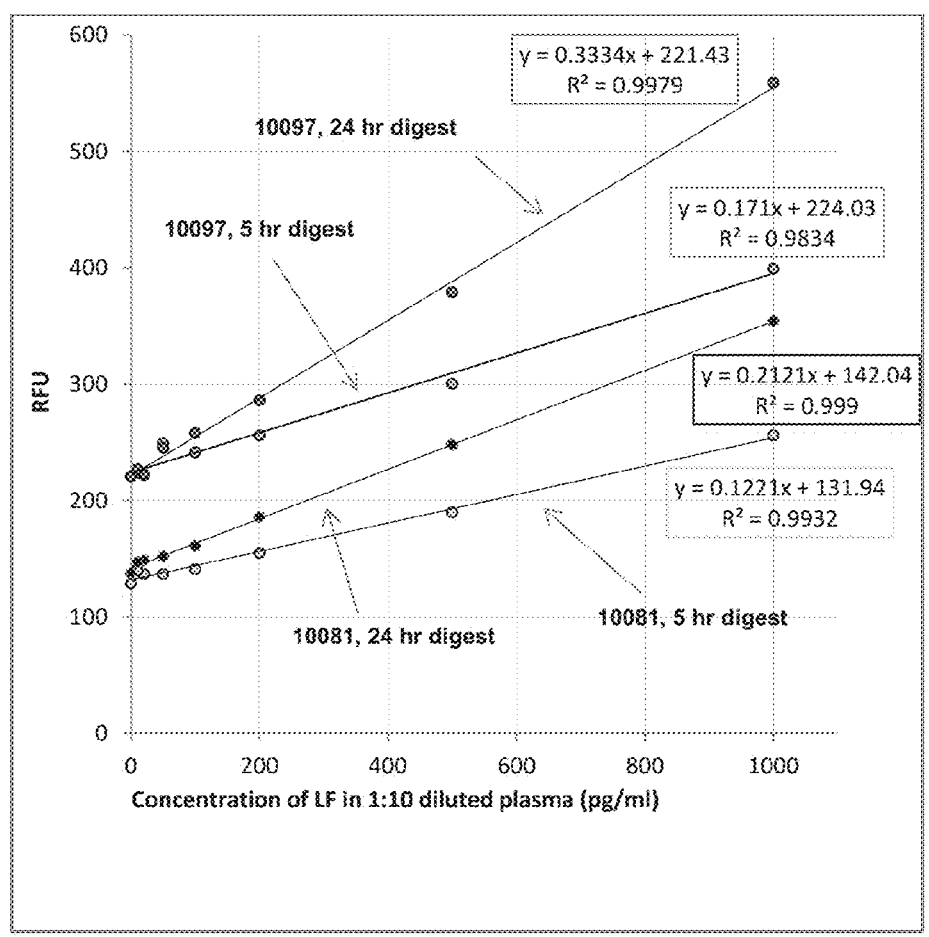
FIG. 8 is a graph showing measured fluorescence of the cleavage products of LF-specific peptide substrates cleaved by LF in diluted plasma samples, according to embodiments of the present disclosure.

In this simpler method the substrate was added directly to diluted plasma in replicate microplate wells and the fluorescence was monitored hourly. A plot of the cleavage of 1.25 µM LBL 10081 at 5 hrs and 24 hrs as a function of LF concentration is shown in FIG. 8. Likewise, the results obtained for LBL 10097 cleavage at 5 hrs and 24 hrs as a function of LF concentration are also shown in FIG. 8. For these assays a 1:10 dilution of the plasma was used. Each RFU value for wells containing LF represented the average of 4 replicate wells and 3 reads of the plate. Each value for wells containing no LF was the average of 12 replicate wells and 3 reads of the plate. For LBL 10081, the amount of cleaved peptide was linearly proportional to the amount of LF present in the diluted plasma from 10 to 1000 pg LF/ml of diluted plasma.

FIG. 8: LBL 10081 cleavage at 5 hrs and 24 hrs (black circles), and LBL 10097 cleavage at 5 hrs and 24 hrs, and LBL 10097 cleavage at 5 hrs and 24 hrs as a function of LF concentration in 1:10 diluted plasma.

As with the HPLC method, the limit of detection was calculated from the normal distribution (2.7 standard deviations) of blank samples (n=12) (Table 4). The limit of detection for both peptide substrates after 5 hrs and 24 hrs digestions was approximately 1 ng LF/ml neat plasma (Table 4).

TABLE 4

Digestion of LBL 10097 and LBL 10081 by different concentrations of LF.

| LF (pg/ml) in 1:10 diluted plasma | Substrate RFUs after 5 hrs digest | | Substrate RFUs after 24 hrs digest | |
|---|---|---|---|---|
| | 10097 | 10081 | 10097 | 10081 |
| 1000 | 399 | 256 | 559 | 354 |
| 500 | 301 | 190 | 379 | 248 |
| 200 | 256 | 155 | 286 | 186 |
| 100 | 242 | 141 | 258 | 161 |
| 50 | 249 | 137 | 245 | 152 |
| 20 | 222 | 137 | 223 | 149 |
| 10 | 224 | 140 | 227 | 147 |
| 0 | 221 | 129 | 221 | 138 |
| Standard deviation of the blanks | 8.69 | 7.29 | 7.53 | 7.50 |
| LOD (pg/ml of 1:10 diluted plasma) | 120 | 60 | 139 | 77 |
| LOD × 10 (pg/ml) neat plasma | 1200 | 600 | 1390 | 770 |

Kinetic Analysis of the LF Activity Using the Microplate Assay.

Figure 9:
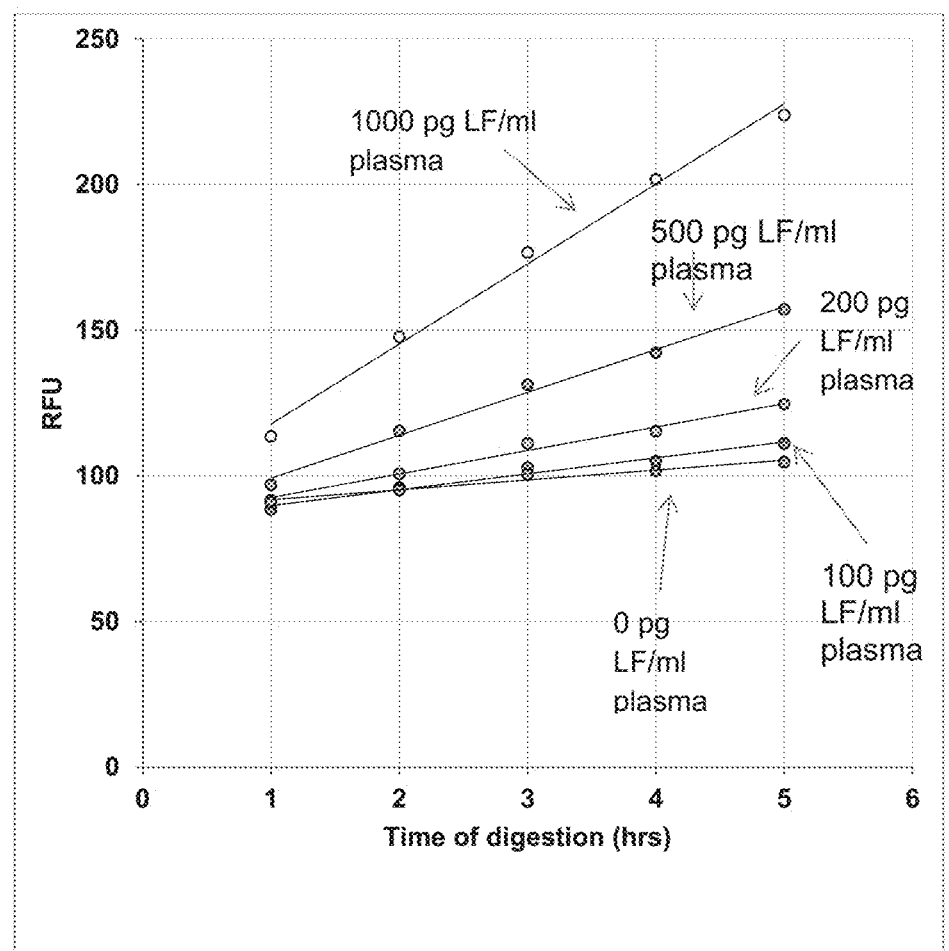
FIG. 9 is a graph showing measured fluorescence as a function of time of LF-specific peptide substrates cleaved by LF in diluted plasma samples, according to embodiments of the present disclosure.
Figure 10:
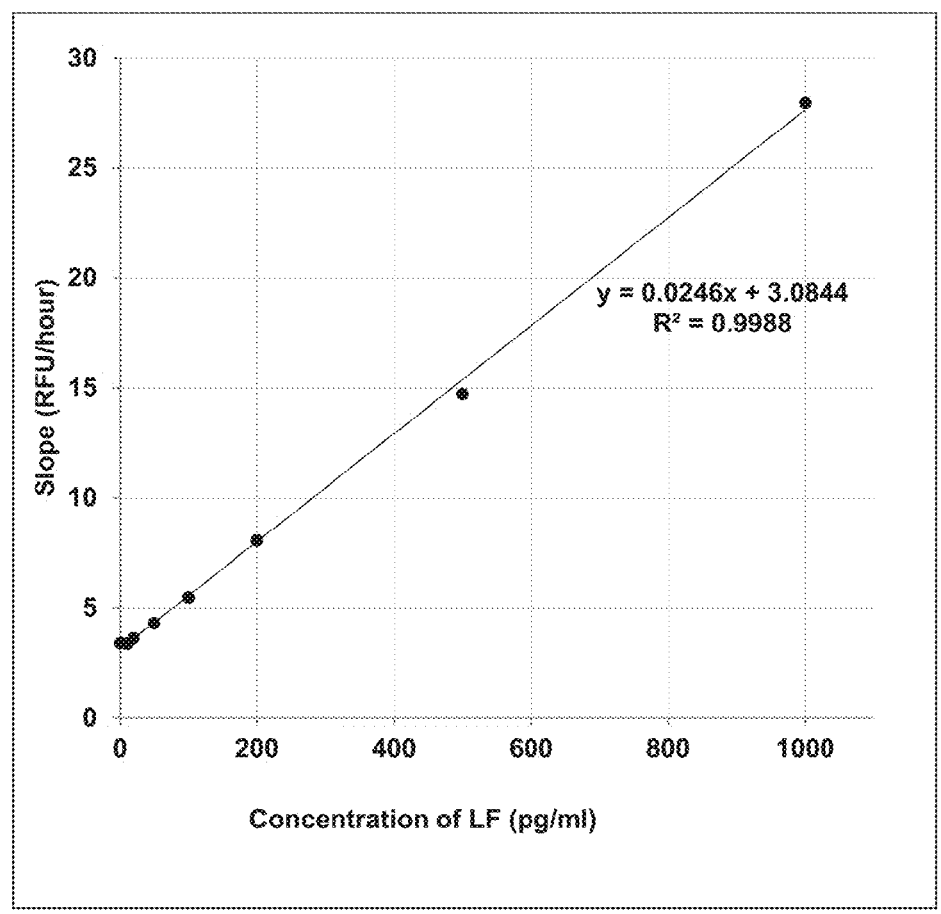
FIG. 10 is a graph showing the relationship between the slope of fluorescence change over time and LF concentration, according to embodiments of the present disclosure.

The data described above was for a single endpoint after 5 hours digestion by LF in 1:10 diluted plasma. This resulted in a limit of detection around 1 ng LF/ml in neat plasma using LBL 10081. Subsequently, the digestion of LBL 10081 by LF in the diluted plasma was repeated 6 times. A kinetic analysis of the data where the cleavage of LBL 10081 as a function of time for each concentration of LF is shown in Table 5. The data presented were the averages of 6 data sets, each with 4 replicates for each sample which contained LF and 12 blank replicates per data set and 3 plate reads at each time point. A plot of the fluorescence (RFU) as a function of time of digestion for individual LF concentrations (pg/ml) is shown in FIG. 9. The slopes of the curves at each concentration (see Table 5 last row) could be plotted as a function of the concentration of LF and the resulting slope was then used to determine the amount of LF present in unknown samples (FIG. 10). The advantage of using the kinetic data is that any differences in the background observed for different sources of plasma are accommodated by this method.

FIG. 9: Cleavage of LBL 10081 by a series of concentrations of LF (pg/ml) in 1:10 diluted plasma as a function of time.

FIG. 10: Slope in RFU/hour as a function of concentration of LF in 1:10 diluted plasma.

TABLE 5

Digestion of LBL 10081 by different concentrations of LF in 1:10 diluted plasma as a function of time.

| Time (hours) | Substrate RFUs for LF (pg/ml) | | | | | | | |
|---|---|---|---|---|---|---|---|---|
| | 1000 | 500 | 200 | 100 | 50 | 20 | 10 | 0 |
| 1 | 114 | 97 | 92 | 88 | 88 | 87 | 89 | 91 |
| 2 | 148 | 116 | 101 | 96 | 95 | 93 | 94 | 95 |
| 3 | 177 | 131 | 111 | 103 | 100 | 99 | 98 | 101 |
| 4 | 202 | 142 | 115 | 105 | 102 | 99 | 100 | 102 |
| 5 | 224 | 157 | 125 | 111 | 106 | 102 | 103 | 105 |
| Slope (RFU/hr) | 27.48 | 14.72 | 8.06 | 5.46 | 4.30 | 3.61 | 3.35 | 3.39 |

The slope was 0.0246 RFU/hr/pg/ml. The limit of detection, determined from the average standard deviation for the slopes obtained for the 6 blanks times 3, was 80 pg/ml. This was equivalent to 800 pg LF/ml in neat plasma.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. An anthrax lethal factor-specific peptide substrate comprising an amino acid sequence of the formula $X^1$-$X^2$-$X^3$-$X^4$-$X^5$-$X^6$-$X^{7*}$ (SEQ ID NO:8), wherein $X^1$ is either present or absent, and when present, is Arg;
$X^2$ is Arg;
$X^3$ is Lys;
$X^4$ is Lys;
$X^5$ is Val;
$X^6$ is Tyr; and
$X^{7*}$ has the formula $X^7$—Z, where
$X^7$ is Pro, and
Z is a detectable label covalently linked by an amide linkage or an ester linkage to an alpha carboxyl group of $X^7$, and wherein at least one of $X^1$, $X^2$, $X^3$ and $X^4$, is a D isomer of the amino acid.

2. The peptide substrate of claim 1, wherein at least two of $X^1$, $X^2$, $X^3$ and $X^4$, are a D isomers of the amino acid.

3. The peptide substrate of claim 1, wherein at least three of $X^1$, $X^2$, $X^3$, and $X^4$, are a D isomer of the amino acid.

4. The peptide substrate of claim 1, wherein $X^2$ is D-Arg; $X^3$ is D-Lys; and $X^4$ is D-Lys.

5. The peptide substrate of claim 4, wherein $X^1$ is present and is D-Arg.

6. The peptide substrate of claim 1, wherein the number of amino acids in the substrate is less than 9.

7. The peptide substrate of claim 1, wherein the detectable label comprises a fluorogenic or chromogenic moiety.

8. The peptide substrate of claim 1, wherein the detectable label comprises a coumarin, a rhodamine, or an aromatic dye.

9. The peptide substrate of claim 1, wherein the detectable label is 7-amido-4-methylcoumarin, 7-amido-4-trifluoromethylcoumarin, 7-amido-4-carbamoylmethylcoumarin, p-nitroanilide, or p-nitrophenyl ester.

10. The peptide substrate of claim 1, wherein Z is 7-amido-4-methylcoumarin.

11. The peptide substrate of claim 1, wherein the peptide substrate is of 6 to 100 amino acids in length.

12. The peptide substrate of claim 1, wherein the peptide substrate is of 6 to 50 amino acids in length.

13. The peptide substrate of claim 1, wherein the peptide substrate is of 6 to 20 amino acids in length.

14. A kit for detecting anthrax lethal factor in a biological sample, the kit comprising:

an anthrax lethal factor-specific peptide substrate of claim 1; and
a standardization element.

15. The kit of claim 14, wherein the standardization element comprises one or more positive reference samples, each comprising a known amount of anthrax lethal factor.

16. The kit of claim 14, wherein the standardization element comprises a negative reference sample that does not comprise anthrax lethal factor.

17. The kit of claim 14, wherein the standardization element comprises a standardization chart or table for converting one or more measured levels of a cleavage product of the peptide substrate to a concentration of lethal factor.

18. The kit of claim 14, wherein the kit further comprises a peptide substrate-specific assay buffer.

19. The kit of claim 14, wherein the kit further comprises an anthrax lethal factor enrichment element configured to enrich lethal factor in a biological sample when the biological sample is contacted with the element.

20. The kit of claim 19, wherein the anthrax lethal factor enrichment element comprises a anthrax lethal factor-specific binding partner bound to a solid support, wherein the anthrax lethal factor-specific binding partner is configured to bind anthrax lethal factor in a biological sample when the biological sample is contacted with the element.

21. The kit of claim 20, wherein the anthrax lethal factor-specific binding partner comprises an antibody or anthrax protective antigen 63 (PA63).

22. The kit of claim 20, wherein the solid support is a bead, a column or a multi-well plate.

23. The kit of claim 14, wherein at least three of $X^1$, $X^2$, $X^3$ and $X^4$ is a D isomer of the amino acid.

24. The peptide substrate of claim 14, wherein $X^1$ is Arg, $X^2$ is D-Arg, $X^3$ is D-Lys, $X^4$ is D-Lys, $X^5$ is Val, $X^6$ is Tyr, and $X^7$ is Pro.

* * * * *